(12) United States Patent
Cho et al.

(10) Patent No.: US 11,730,695 B2
(45) Date of Patent: *Aug. 22, 2023

(54) COMPOSITION FOR ALLEVIATING FACIAL REDNESS, COMPRISING STEM CELL-DERIVED EXOSOMES AS ACTIVE INGREDIENT

(71) Applicant: ExoCoBio Inc., Seoul (KR)

(72) Inventors: Byong Seung Cho, Gunpo-si (KR); Yong Weon Yi, Seoul (KR); Kwang Ii Kim, Goyang-si (KR)

(73) Assignee: ExoCoBio Inc., Seoul (KR)

( * ) Notice: Subject to any disclaimer, the term of this patent is extended or adjusted under 35 U.S.C. 154(b) by 90 days.

This patent is subject to a terminal disclaimer.

(21) Appl. No.: 17/104,731

(22) Filed: Nov. 25, 2020

(65) Prior Publication Data

US 2021/0077379 A1    Mar. 18, 2021

Related U.S. Application Data

(63) Continuation of application No. PCT/KR2019/005680, filed on May 11, 2019.

(30) Foreign Application Priority Data

May 31, 2018  (KR) .......................... 10-2018-0062707
Feb. 19, 2019  (KR) .......................... 10-2019-0019141

(51) Int. Cl.

| | |
|---|---|
| *A61K 8/98* | (2006.01) |
| *A61K 8/02* | (2006.01) |
| *A61K 8/73* | (2006.01) |
| *A61K 8/60* | (2006.01) |
| *A61N 1/04* | (2006.01) |
| *A61K 8/67* | (2006.01) |
| *A61Q 19/00* | (2006.01) |
| *A61K 8/46* | (2006.01) |

(52) U.S. Cl.
CPC ............. *A61K 8/981* (2013.01); *A61K 8/0212* (2013.01); *A61K 8/46* (2013.01); *A61K 8/60* (2013.01); *A61K 8/671* (2013.01); *A61K 8/676* (2013.01); *A61K 8/735* (2013.01); *A61N 1/0428* (2013.01); *A61Q 19/00* (2013.01)

(58) Field of Classification Search
CPC ......... A61K 8/981; A61K 8/14; A61K 9/0014
See application file for complete search history.

(56) References Cited

U.S. PATENT DOCUMENTS

| | | | | |
|---|---|---|---|---|
| 5,203,768 A | * | 4/1993 | Haak .................... | A61N 1/0448 604/20 |
| 6,048,545 A | * | 4/2000 | Keller ..................... | A61N 1/30 604/20 |
| 9,180,098 B2 | | 11/2015 | Hafner et al. | |
| 2005/0004550 A1 | * | 1/2005 | Sun .......................... | A61N 1/30 977/932 |
| 2010/0297231 A1 | | 11/2010 | Vehring et al. | |
| 2013/0259896 A1 | | 10/2013 | Khandke et al. | |
| 2013/0315987 A1 | | 11/2013 | Lu | |
| 2014/0087001 A1 | * | 3/2014 | Vesey ...................... | A61P 17/12 435/267 |
| 2015/0024011 A1 | * | 1/2015 | Lim ...................... | A61K 9/0019 424/520 |
| 2016/0367660 A1 | | 12/2016 | Hafner et al. | |
| 2017/0087187 A1 | | 3/2017 | Chang et al. | |
| 2017/0152484 A1 | * | 6/2017 | Cho ....................... | A61K 8/361 |
| 2017/0209365 A1 | | 7/2017 | Cho et al. | |
| 2018/0332951 A1 | | 11/2018 | Jang et al. | |
| 2019/0030079 A1 | | 1/2019 | Cho et al. | |
| 2020/0121722 A1 | | 4/2020 | Yl et al. | |
| 2020/0323768 A1 | | 10/2020 | Yi et al. | |
| 2020/0329697 A1 | | 10/2020 | Kim et al. | |

FOREIGN PATENT DOCUMENTS

| | | | |
|---|---|---|---|
| CN | 1160582 A | | 10/1997 |
| CN | 104382827 A | * | 3/2015 |
| CN | 106701672 A | | 5/2017 |
| CN | 107006452 A | | 8/2017 |
| EP | 3 199 175 A1 | | 8/2017 |
| EP | 3 363 817 A1 | | 8/2018 |
| JP | 2012-136518 A | | 7/2012 |
| JP | 2015-057383 A | | 3/2015 |
| JP | 2015-78177 A | | 4/2015 |
| KR | 10-2015-0108795 A | | 9/2015 |
| KR | 10-1663912 B1 | | 10/2016 |
| KR | 10-2017-0089404 A | | 8/2017 |
| KR | 10-2018-0042217 A | | 4/2018 |

(Continued)

OTHER PUBLICATIONS

Exosome d.m.s.c. (https://blog.naver.com/restemkorea/220516198077, 2015) (Year: 2015).*
Harrison et al (Methods, 2002, vol. 28, pp. 14-19) (Year: 2002).*
Kafi et al (JAMA Dermatology, 2007, vol. 143, pp. 606-612) (Year: 2007).*
CN-104382827-A (Espacenetenglish translation, downloaded Apr. 2022) (Year: 2022).*
BioSpace (Regeneus US Patent Allowed for Sygenus Secretions Technology for Acne, Jul. 2017, https://www.biospace.com/article/releases/regeneus-u-s-patent-allowed-for-sygenus-secretions-technology-for-acne-/). (Year: 2017).*
Hu et al (Scientific Reports, Sep. 2016, vol. 6, pp. 1-11) (Year: 2016).*
El-Domyati et al (Journal Cosmet Dermatol, 2012, vol. 11, pp. 122-130) (Year: 2012).*

(Continued)

*Primary Examiner* — Mark V Stevens
(74) *Attorney, Agent, or Firm* — Sughrue Mion, PLLC

(57) ABSTRACT

A composition for alleviating facial redness containing stem cell-derived exosomes as an active ingredient and a method of reducing facial redness are provided. When a facial skin is treated with the composition for alleviating facial redness containing stem cell-derived exosomes as an active ingredient, the composition exhibits an excellent effect on skin care by reducing the redness of the face and improving the appearance of the face.

36 Claims, 33 Drawing Sheets

(56) References Cited

FOREIGN PATENT DOCUMENTS

| KR | 10-2019-0069301 | A |   | 6/2019 |   |
|---|---|---|---|---|---|
| WO | 96/09037 | A1 |   | 3/1996 |   |
| WO | 98/36736 | A1 |   | 8/1998 |   |
| WO | 2008/040556 | A1 |   | 4/2008 |   |
| WO | 2010/148337 | A1 |   | 12/2010 |   |
| WO | 2016/197196 | A1 |   | 12/2016 |   |
| WO | 2017/015622 | A2 |   | 1/2017 |   |
| WO | 2017/020034 | A1 |   | 2/2017 |   |
| WO | 2017/122095 | A1 |   | 7/2017 |   |
| WO | WO-2017173150 | A1 | * | 10/2017 | ............ A61K 35/12 |
| WO | 2018/027075 | A1 |   | 2/2018 |   |
| WO | 2018/050872 | A1 |   | 3/2018 |   |
| WO | 2018/053004 | A2 |   | 3/2018 |   |
| WO | 2018/070939 | A1 |   | 4/2018 |   |
| WO | 2018/078524 | A1 |   | 5/2018 |   |

OTHER PUBLICATIONS

Ho Seong Jeon, "Improved Stability of Sterically Stabilized Liposomal Preparations by Lyophilization", Master's Thesis. Graduate School of Chung-ang University, Dec. 2000.
International Search Report of PCT/KR2019/008850 dated Oct. 24, 2019 [PCT/ISA/210].
International Search Report of PCT/KR2019/008832 dated Oct. 29, 2019 [PCT/ISA/210].
Bosch et al., "Trehalose prevents aggregation of exosomes and cryodamage", Scientific Reports, 2016, vol. 6, No. 36162, pp. 1-11 (12 pages total).
Naver Blog, "Get a regeneration care by Exosome Original Repair ampule after Fraxel treatment /Stem Cell ampule / Fraxel treatment", Oct. 22, 2015, pp. 1-8, https://blog.naver.com/restemkorea/220516198077.
International Search Report of PCT/KR2019/005680 dated Aug. 16, 2019 [PCT/ISA/210].

* cited by examiner

COMPOSITION FOR ALLEVIATING FACIAL REDNESS, COMPRISING STEM CELL-DERIVED EXOSOMES AS ACTIVE INGREDIENT

CROSS REFERENCE

This application is a Bypass Continuation of International Application No. PCT/KR2019/005680 filed May 11, 2019, claiming priority based on Korean Patent Application No. 10-2018-0062707 filed May 31, 2018 and Korean Patent Application No. 10-2019-0019141 filed Feb. 19, 2019, the entire contents of which are incorporated herein by reference.

TECHNICAL FIELD

The present invention relates to a composition for alleviating facial redness containing stem cell-derived exosomes as an active ingredient.

Moreover, the present invention relates to a method of reducing facial redness using the composition for alleviating facial redness.

BACKGROUND ART

Human skin contains blood vessels distributed therein. The human facial skin is thin and has a large number of blood vessels, and thus it turns red more easily than other areas. In general, the phenomenon in which the facial skin becomes abnormally red is referred to as "facial redness". Facial redness is regarded as a skin aesthetic problem and may be caused by very diverse factors.

Facial redness is a symptom that often occurs in menopausal women as their face flashes, but it may also be caused by sunlight, heat, stress, weather, food, hot baths, drugs, or the like. When facial redness worsens, it may lead to serious skin diseases such as rosacea and telangiectasia.

In order to treat or alleviate facial redness, hormone therapy, a method of changing lifestyle or environment and the like have been proposed. However, the hormone therapy has problems that it causes side effects and the treatment effects thereof differ depending on persons. In addition, in the method of changing lifestyle or environment, considerable effort and time are required to obtain a satisfactory effect of alleviating facial redness.

In recent years, studies have been actively conducted on the development of agents for alleviating facial redness using natural substances. In the case of compositions for alleviating facial redness, which are manufactured using these natural substances, the amount of content of an active ingredient in the natural extract is low, and hence a large amount of the natural extract needs to be used to obtain a certain effect of alleviating facial redness. In the majority of cases, the fact that these compositions are based on natural substances has been emphasized in marketing, but there is a need for more scientific research on the practical efficacies of natural substances on the effect of alleviating facial redness. In addition, functional cosmetics for alleviating facial redness containing a plant extract as an active ingredient have problems that they may cause a foreign body sensation during their evaporation after application to the skin, and the duration of the effect thereof is short.

Recently, there have been reports that cell secretomes contain various bioactive molecules that regulate cellular behaviors. In particular, cell secretomes contain 'exosome' that has intercellular signaling functions, and thus studies on the components and functions thereof have been actively conducted.

Cells secrete various membranous vesicles to their extracellular environment, and these released vesicles are usually called extracellular vesicles (EVs). The EV is also called cell membrane-derived vesicle, ectosome, shedding vesicle, microparticle, exosome, etc., and is also used discriminately from exosome in some cases.

Exosome is a vesicle of tens to hundreds of nanometers in size, which consists of a phospholipid bilayer membrane having the same structure as that of the cell membrane. This exosome contains proteins, nucleic acids (mRNA, miRNA, etc.) and the like which are called exosome cargo. It is known that exosome cargo includes a wide range of signaling factors, and these signaling factors are specific for cell types and regulated differently depending on secretory cells' environment. It is known that exosome is an intercellular signaling mediator secreted by cells, and various cellular signals transmitted through it regulate cellular behaviors, including the activation, growth, migration, differentiation, dedifferentiation, apoptosis, and necrosis of target cells. Exosome contains specific genetic materials and bioactive factors depending on the nature and state of cells from which the exosome was derived. Exosome derived from proliferating stem cells regulates cell behaviors such as cell migration, proliferation and differentiation, and recapitulates the function of stem cells involved in tissue regeneration (Nature Review Immunology 2002 (2) 569-579).

However, although various studies of exosomes have been conducted, which suggest the possibility for the treatment of some diseases using exosomes, not much attention has been paid to the development of new formulations which can stably maintain and make exosomes stored, and the linking of exosomes with various medical or aesthetic technologies for increasing the convenience and efficacy of exosomes.

The present inventors have conducted extensive studies on new applications of stem cell-derived exosomes and on the application of these exosomes to medical or aesthetic technology, and as a result, have found that, when a face is treated with a composition containing stem cell-derived exosomes as an active ingredient, the redness of the face is reduced, thereby completing the present invention.

Meanwhile, it is to be understood that the matters described as the background art are intended merely to aid in the understanding of the background of the present invention and are not admitted as prior art against the present invention.

SUMMARY OF INVENTION

An object of the present invention is to provide a composition for alleviating facial redness containing stem cell-derived exosomes as an active ingredient.

Another object of the present invention is to provide a functional cosmetic composition and skin external preparation for alleviating facial redness containing the composition.

Still another object of the present invention is to provide a method of reducing facial redness by using the composition for alleviating facial redness.

However, the objects of the present invention as described above are illustrative and the scope of the present invention is not limited thereby. In addition, other objects and advantages of the present invention will be more apparent from the following description, the appended claims and the accompanying drawings.

DETAILED DESCRIPTION OF INVENTION

To achieve the above objects, the present invention provides a composition for alleviating facial redness containing stem cell-derived exosomes as an active ingredient, and a method of reducing facial redness using the same.

As used herein, the term "exosomes" refers to vesicles of tens to hundreds of nanometers in size (preferably, about 30 to 200 nm), which consist of a phospholipid bilayer membrane having the same structure as that of the cell membrane (however, the particle size of exosomes is variable depending on the type of cell from which the exosomes are isolated, an isolation method and a measurement method) (Vasiliy S. Chernyshev et al., "Size and shape characterization of hydrated and desiccated exosomes", Anal Bioanal Chem, (2015) DOI 10.1007/s00216-015-8535-3). These exosomes contain proteins, nucleic acids (mRNA, miRNA, etc.) and the like which are called exosome cargo. It is known that exosome cargo includes a wide range of signaling factors, and these signaling factors are specific for cell types and regulated differently depending on secretory cells' environment. It is known that exosomes are intercellular signaling mediators secreted by cells, and various cellular signals transmitted through them regulate cellular behaviors, including the activation, growth, migration, differentiation, dedifferentiation, apoptosis, and necrosis of target cells.

Meanwhile, the term "exosomes" as used herein is intended to include all vesicles (e.g., exosome-like vesicles) which are secreted from stem cells and released into extracellular spaces, and have a nano-sized vesicle structure and a composition similar to that of exosomes. The stem cells are not limited to the kind thereof, but may preferably be mesenchymal stem cells, for example, adipose-, bone marrow-, umbilical cord- or umbilical cord blood-derived stem cells, more preferably adipose-derived stem cells. The adipose-derived stem cells are not limited to the kind thereof as long as they have no risk of infection with pathogens and do not cause immune rejection, but may preferably be human adipose-derived stem cells.

However, as exosomes used in the present invention, various exosomes that are being used in the art or may be used in the future may, of course, be used as long as they have an effect for alleviating facial redness and do not cause adverse effects on the human body. Therefore, it should be noted that exosomes isolated according to the isolation method of Examples described below should be understood as an example of exosomes that may be used in the present invention, and the present invention is not limited thereto.

As used herein, the term "iontophoresis" refers to a method of flowing a microcurrent through a skin to which an active ingredient has been applied, generating a potential difference thereby and changing the electrical environment of the skin, and thus allowing an ionized active ingredient to penetrate the skin by electrical repulsion. Examples of iontophoresis that is used in one embodiment of the present invention include: a method of introducing a microcurrent into a skin by allowing the microcurrent to flow from an external power source into an electrode patch on the skin, the microcurrent generated by the external power source; a method of introducing a microcurrent into a skin, the microcurrent generated by a battery provided in an electrode patch on the skin; and a method of introducing a microcurrent into a skin through a patch on the skin provided with a reverse electrodialysis device, the microcurrent generated by the concentration difference between high concentration electrolyte solution and low concentration electrolyte solution in the reverse electrodialysis device. However, the present invention is not limited thereto, and various types of iontophoresis may, of course, be used.

The composition for alleviating facial redness according to one embodiment of the present invention comprises stem cell-derived exosomes as an active ingredient.

The composition may contain a lyophilized formulation comprising: as active ingredients, stem cell-derived exosomes; and methionine, mannitol, and trehalose. For example, the weight ratio of methionine, mannitol and trehalose in the lyophilized formulation may be 1:1:1.

In the composition, the lyophilized formulation may further comprise ascorbic acid and retinol. For example, the weight ratio of methionine, mannitol, trehalose, ascorbic acid and retinol in the lyophilized formulation may be 9:9:9:0.5:0.5.

The composition may comprise the lyophilized formulation and a diluent. For example, the diluent may be water for injection, physiological saline, phosphate buffered saline, purified water, or deionized water. In addition, the diluent may further comprise hyaluronic acid or hyaluronate (e.g., sodium hyaluronate). For example, the composition may be prepared as a suspension.

In one embodiment of the present invention, the composition may be administered by microneedling, iontophoresis or injection.

In one embodiment of the present invention, the composition may be a pharmaceutical composition, a cosmetic composition or a skin external preparation. For example, the composition may be prepared as an injectable formulation.

In one embodiment of the present invention, when the composition for alleviating facial redness is used as a pharmaceutical composition, it may include pharmaceutically acceptable carriers, excipients or diluents. The carriers, excipients and dilutes include, but are not limited to, lactose, dextrose, trehalose, sucrose, sorbitol, mannitol, xylitol, erythritol, maltitol, starch, acacia gum, alginate, gelatin, calcium phosphate, calcium carbonate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. In addition, the effective amount of the pharmaceutical composition according to one embodiment of the present invention means the amount required for administration in order to achieve an effect for alleviating facial redness.

The content of the pharmaceutical composition according to one embodiment in a formulation may be suitably selected depending on the kind, amount, form and the like of additional components as described above. For example, the pharmaceutical composition of the present invention may be contained in an amount of about 0.1 to 99 wt %, preferably about 10 to 90 wt %, based on the total weight of an injectable formulation. Furthermore, the suitable dose of the pharmaceutical composition according to one embodiment of the present invention may be adjusted depending on the severity of facial redness, the type of formulation, formulating method, patient's age, sex, body weight, health condition, diet, excretion rate, the period of administration, and the regime of administration. For example, when the pharmaceutical composition according to one embodiment of the present invention is administered to an adult, it may be administered once to several times at a dose of 0.001 mg/kg to 100 mg/kg per day.

Meanwhile, when the composition for alleviating facial redness according to one embodiment of the present invention is prepared as a skin external preparation and/or a cosmetic composition, it may suitably contain components which are generally used in cosmetic products or skin external preparations, for example, moisturizers, antioxidants, oily components, UV absorbers, emulsifiers, surfactants, thickeners, alcohols, powder components, colorants, aqueous components, water, and various skin nutrients, etc., as needed, within the range that does not impair the effect of the present invention.

Furthermore, the skin external preparation and/or cosmetic composition according to one embodiment of the present invention may comprise, in addition to stem cell-derived exosomes, an agent for improving skin condition and/or a moisturizer, which has been used in the prior art, within the range that does not impair the effects (e.g., an effect for alleviating facial redness) thereof. For example, stem cell-derived exosomes may be contained in or mixed with at least one of hydrogel, hyaluronic acid, salt of hyaluronic acid (e.g., sodium hyaluronate, etc.), or hyaluronate gel. In the skin external preparation and/or cosmetic composition according to one embodiment of the present invention, the kind of hydrogel is not particularly limited, but the hydrogel may be preferably obtained by dispersing a gelled polymer in a polyhydric alcohol. The gelled polymer may be at least one selected from the group consisting of pluronic, purified agar, agarose, gellan gum, alginic acid, carrageenan, *cassia* gum, xanthan gum, galactomannan, glucomannan, pectin, cellulose, guar gum, and locust bean gum, and the polyhydric alcohol may be at least one selected from the group consisting of ethylene glycol, propylene glycol, 1,3-butylene glycol, isobutylene glycol, dipropylene glycol, sorbitol, xylitol, and glycerin.

The skin external preparation and/or cosmetic composition according to one embodiment of the present invention may be used in various forms, for example, patches, mask packs, mask sheets, creams, tonics, ointments, suspensions, emulsions, pastes, lotions, gels, oils, packs, sprays, aerosols, mists, foundations, powders, and oilpapers. For example, the skin external preparation and/or cosmetic composition may be applied to or soaked in at least one surface of a patch, a mask pack or a mask sheet.

The cosmetic composition according to one embodiment of the present invention is used for the purpose of alleviating facial redness, and the cosmetic composition may be prepared as any formulation which is generally prepared in the art. For example, it may be formulated as patch, mask pack, mask sheet, skin softener, nutrition, astringent lotion, nourishing cream, massage cream, eye cream, cleansing cream, essence, eye essence, cleansing lotion, cleansing foam, cleansing water, sunscreen, lipstick, soap, shampoo, surfactant-containing cleanser, bath preparation, body lotion, body cream, body oil, body essence, body cleanser, hairdye, hair tonic, etc., but is not limited thereto.

The skin external preparation and/or cosmetic composition according to one embodiment of the present invention contains components which are commonly used in skin external preparations and/or cosmetic products. For example, the skin external preparation and/or cosmetic composition may contain conventional adjuvants and carriers, such as antioxidants, stabilizers, solubilizers, vitamins, pigments, and fragrances. In addition, other components in each formulation for the skin external preparation and/or cosmetic composition may be suitably selected without difficulty by those skilled in the art depending on the type or intended use of skin external preparation and/or cosmetic composition.

The present invention also provides a method of preventing, suppressing, alleviating, ameliorating or treating facial redness using the composition for alleviating facial redness.

The method of preventing, suppressing, alleviating, ameliorating or treating facial redness according to one embodiment of the present invention comprises steps of: (a) preparing a composition for alleviating facial redness containing stem cell-derived exosomes as an active ingredient; and (b) treating a skin of a subject with the composition for alleviating facial redness.

In the method of preventing, suppressing, alleviating, ameliorating or treating facial redness according to one embodiment of the present invention, the composition may be administered to the skin by microneedling, iontophoresis or injection.

The method of preventing, suppressing, alleviating, ameliorating or treating facial redness according to one embodiment of the present invention further includes steps of: (c) performing iontophoresis by allowing a microcurrent to flow through the skin treated with the composition; and (d) delivering the stem cell-derived exosomes inside the skin by the microcurrent.

In the method of preventing, suppressing, alleviating, ameliorating or treating facial redness according to one embodiment of the present invention, the composition may be used in various forms, for example, patches, mask packs, mask sheets, creams, tonics, ointments, suspensions, emulsions, pastes, lotions, gels, oils, packs, sprays, aerosols, mists, foundations, powders, and oilpapers. For example, the composition may be applied to or soaked in at least one surface of a patch, a mask pack or a mask sheet.

In the method of preventing, suppressing, alleviating, ameliorating or treating facial redness according to one embodiment of the present invention, step (b) may be performed by: (b1) applying the composition directly to the skin; or (b2) contacting or attaching a mask pack, a mask sheet or a patch, which has the composition applied thereto or soaked therein, to the skin; or (b3) sequentially performing (b1) and (b2).

In the method of preventing, suppressing, alleviating, ameliorating or treating facial redness according to one embodiment of the present invention, at least one of hydrogel, hyaluronic acid, salts of hyaluronic acid (e.g., sodium hyaluronate, etc.), or hyaluronate gel may be applied to at least one side of the mask pack, mask sheet or patch. The kind of hydrogel is not limited, but the hydrogel may be preferably obtained by dispersing a gelled polymer in a polyhydric alcohol. The gelled polymer and the polyhydric alcohol may be those exemplified in the foregoing.

In the method of preventing, suppressing, alleviating, ameliorating or treating facial redness according to one embodiment of the present invention, step (c) may be performed by contacting or attaching an iontophoresis device to the skin.

In the method of preventing, suppressing, alleviating, ameliorating or treating facial redness according to one embodiment of the present invention, the iontophoresis device may include at least one battery selected from the group consisting of flexible batteries, lithium-ion secondary batteries, alkaline batteries, dry cells, mercury batteries, lithium batteries, nickel-cadmium batteries, and reverse electrodialysis batteries.

Advantageous Effects

When a facial skin is treated with the composition for alleviating facial redness containing stem cell-derived exosomes as an active ingredient according to the present invention, the composition exhibits an excellent effect on skin care by reducing the redness of the face and improving the appearance of the face.

It should be understood that the scope of the present invention is not limited to the aforementioned effects.

BRIEF DESCRIPTION OF DRAWINGS

"FIG. 4A" shows the particle size distribution and the number of particles obtained by tunable resistive pulse sensing (TRPS) analysis. "FIG. 4B" shows the particle size distribution and the number of particles obtained by nanoparticle tracking analysis (NTA). "FIG. 4C" shows different magnifications of particle images obtained by transmitted electron microscopy (TEM) analysis. "FIG. 4D" shows the results of Western blot analysis of exosomes obtained according to one embodiment of the present invention. "FIG. 4E" shows the results of flow cytometry for CD63 and CD81 in the analysis of markers for exosomes obtained according to one embodiment of the present invention.

"FIG. 6A" shows the results obtained when trehalose was added throughout the preparation process; "FIG. 6B" shows the results obtained in the case that conditioned media are freeze-stored and thawed, and then trehalose was added to the thawed media; and "FIG. 6C" shows the results obtained when no trehalose was added.

FIG. 10A is a graph showing the results of measuring the redness under the eyes of subject 1, and FIG. 10B is a graph showing the results of measuring the redness of the cheeks of subject 1.

EXAMPLES

Figure 1:
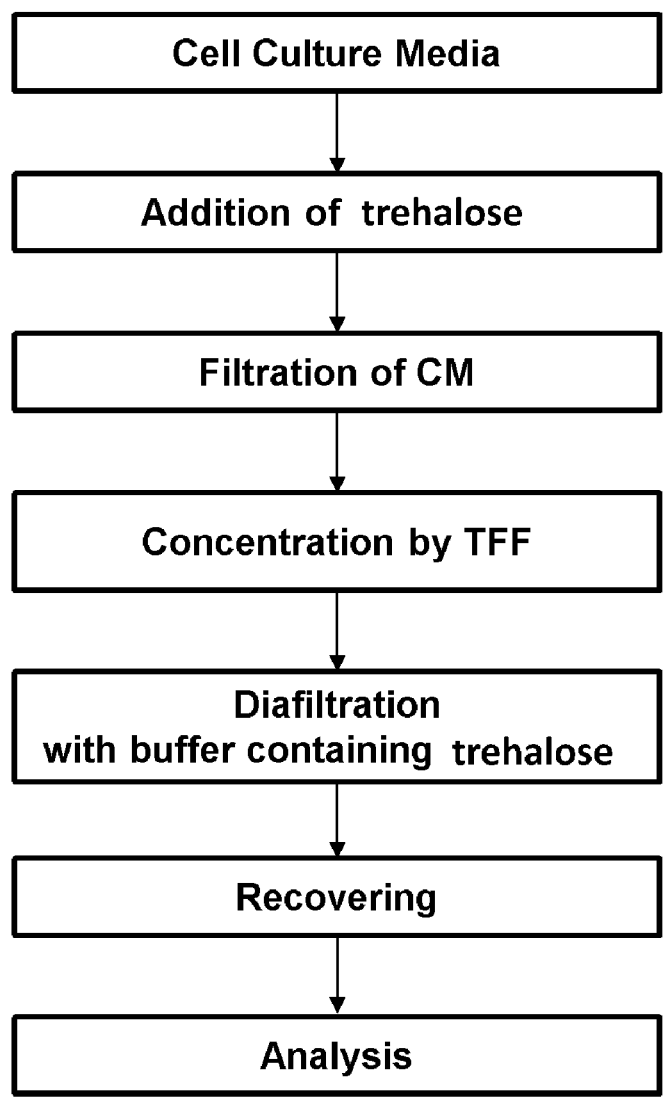
FIG. 1 is a flowchart illustrating a method of isolating and purifying exosomes in a method of preparing exosomes from culture media of stem cells according to one embodiment of the present invention.

Hereinafter, the present invention will be described in more detail with reference to the following examples. However, the following examples are only to illustrate the present invention and are not intended to limit or restrict the scope of the present invention. Those that can be easily inferred by those skilled in the art from the detailed description and examples of the present invention are interpreted as falling within the scope of the present invention. References referred to in the present invention are incorporated herein by reference.

Throughout the present specification, it is to be understood that, when any part is referred to as "comprising" any component, it does not exclude other components, but may further include other components, unless otherwise specified.

Example 1: Cell Culture

Human dermal fibroblast (HDF) Hs68 cells purchased from ATCC were subcultured in DMEM (purchased from ThermoFisher Scientific) medium containing 10% fetal bovine serum (FBS; purchased from ThermoFisher Scientific) and 1% antibiotics-antimycotics (purchased from ThermoFisher Scientific) at 37° C. under 5% $CO_2$.

According to a cell culture method known in the technical field to which the present invention pertains, adipose-derived stem cells were cultured at 37° C. under 5% $CO_2$. Next, the cells were washed with phosphate-buffered saline (purchased from ThermoFisher Scientific), and then the medium was replaced with serum-free, phenol red-free medium, and the cells were cultured for 1 to 10 days. The supernatant (hereinafter, referred to as "conditioned medium") was recovered.

In order to obtain exosomes having a uniform particle size distribution and high purity in an exosome isolation process, 2 wt % of trehalose was added to the conditioned medium. After addition of trehalose, the conditioned medium was filtered through 0.22 μm filter to remove impurities, such as cell debris, waste, macroparticles and the like. From the filtered conditioned medium, exosomes were immediately isolated. In addition, the filtered conditioned medium was stored in a refrigerator (10° C. or below), and then used for exosome isolation. Furthermore, the filtered conditioned medium was freeze-stored in an ultra-low temperature freezer at −60° C. or below, thawed, and then subjected to exosome isolation. Thereafter, exosomes were isolated from the conditioned medium by Tangential Flow Filtration (TFF) method.

Example 2: Isolation and Purification of Exosomes by TFF Method

For isolating, concentrating and diafiltrating exosomes from the conditioned medium filtered through 0.22 μm filter in Example 1, TFF method was used. As a filter for TFF method, a cartridge filter (also known as a hollow fiber filter; purchased from GE Healthcare) or a cassette filter (purchased from Pall, Sartorius, or Merck Millipore) was used. The TFF filter may be selected with various molecular weight cutoffs (MWCOs). Using the filter having selected MWCO, exosomes were isolated and concentrated, and particles, proteins, lipids, nucleic acids, low-molecular-weight compounds, etc., were removed, which are smaller than the MWCO.

To isolate and concentrate exosomes, a TFF filter having MWCO of 100,000 Da (Dalton), 300,000 Da or 500,000 Da was used. Exosomes were isolated from the conditioned medium by removing substances smaller than the MWCO and concentrating the conditioned medium to a volume of about 1/100 to 1/25 by the TFF method.

The isolated and concentrated solution of exosomes was additionally subjected to diafiltration using TFF method. The diafiltration was performed continuously (continuous diafiltration) or discontinuously (discontinuous diafiltration), using a buffer having at least 4 times, preferably at least 6 to 10 times, more preferably at least 12 times volume of the isolated exosomes. To obtain exosomes having a uniform particle size distribution and high purity, 2 wt % trehalose in PBS was added to the buffer. FIGS. 6A to 6E show the results that by the addition of trehalose, exosomes having a uniform particle size distribution and high purity can be obtained in high yield.

Example 3: Analysis of Characteristics of Isolated Exosomes

Figure 2:
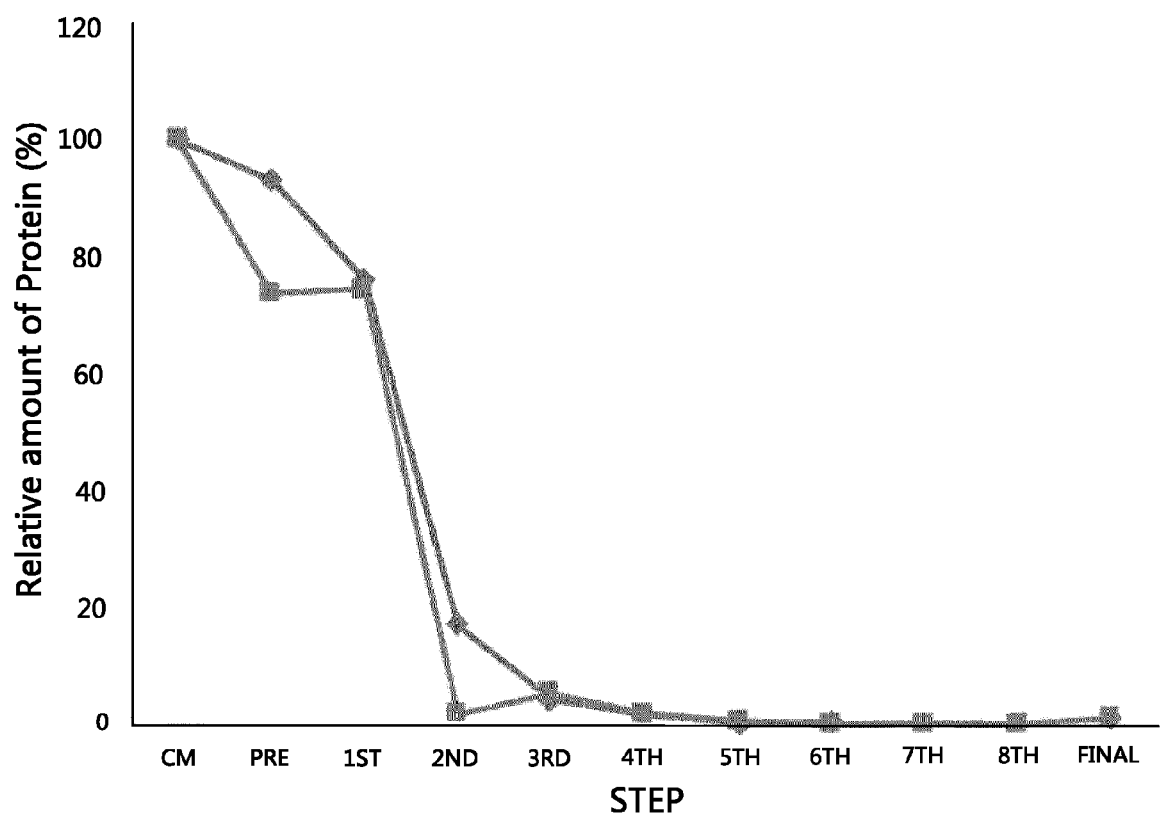
FIG. 2 shows the results of measuring the relative amount of proteins contained in a solution in each step of preparing exosomes from culture media of stem cells according to one embodiment of the present invention. The relative amount of proteins in each step was expressed as the relative ratio of the total amount of proteins in solution of each step to the total amount of proteins in conditioned media of stem cells. The experimental results as shown are the results obtained from two different batches, respectively.

The amounts of proteins of the isolated exosomes, the conditioned medium, and the fractions of TFF isolation process were measured using BCA Protein Assay Kit (purchased from ThermoFisher Scientific) or FluoroProfile Protein Quantification Kit (purchased from Sigma-Aldrich). With regard to exosomes isolated and concentrated by the TFF method according to one embodiment, the extent, to which proteins, lipids, nucleic acids, low-molecular-weight compounds, etc. were removed, was monitored by the protein assays, and the results of the monitoring are shown in FIG. 2. As a result, it could be seen that proteins present in the conditioned medium were very effectively removed by the TFF method according to one embodiment.

Figure 3:
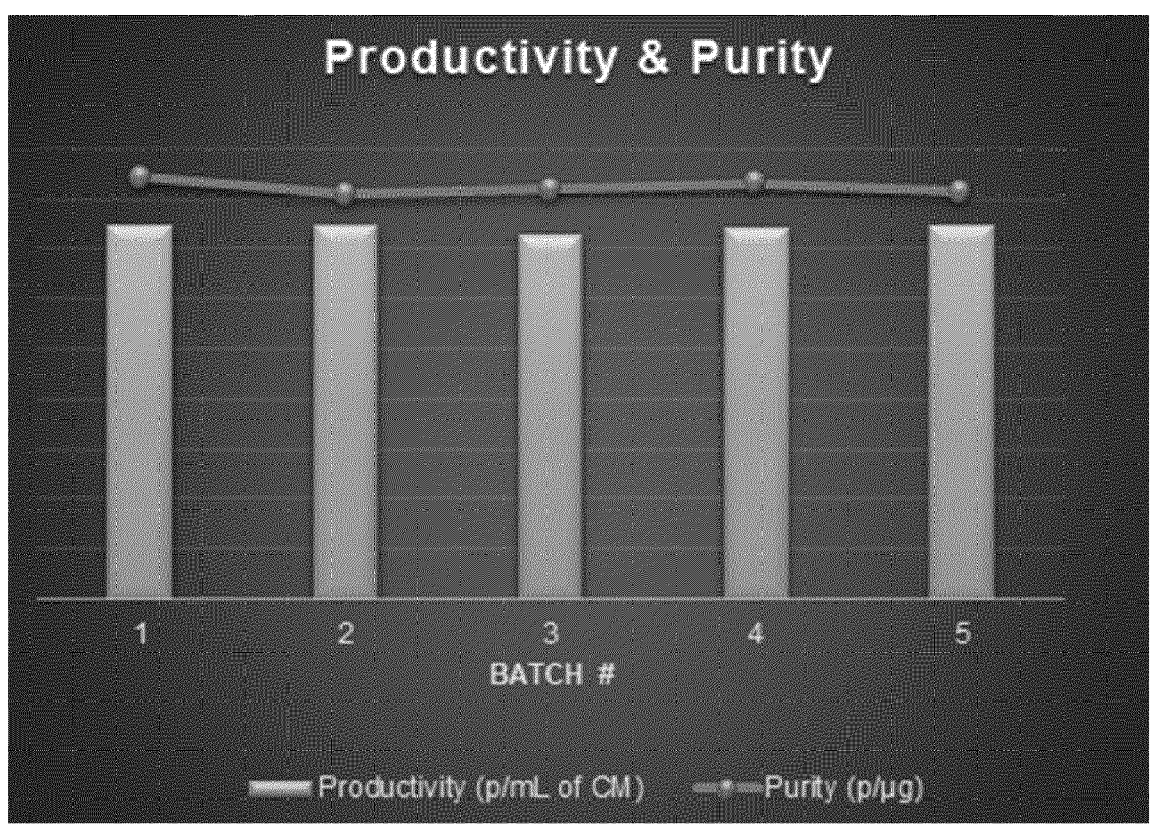
FIG. 3 shows the results of measuring the productivity and purity of exosomes obtained according to one embodiment of the present invention. The productivity of exosomes was calculated as the number of exosome particles obtained per mL of conditioned media of stem cells (CM), and the purity of exosomes was calculated as the number of exosome particles per μg of proteins contained in a final fraction. The experimental results as shown are the results obtained from five different batches, respectively.

FIG. 3 shows the results of comparing the productivity and purity of exosomes in each of five independent batches when exosomes were isolated by the TFF method according to one embodiment of the present invention. The results obtained from the five independent batches were analyzed, and as a result, it was confirmed that exosomes were very reproducibly isolated by the TFF method according to one embodiment of the present invention.

Figure 4A:
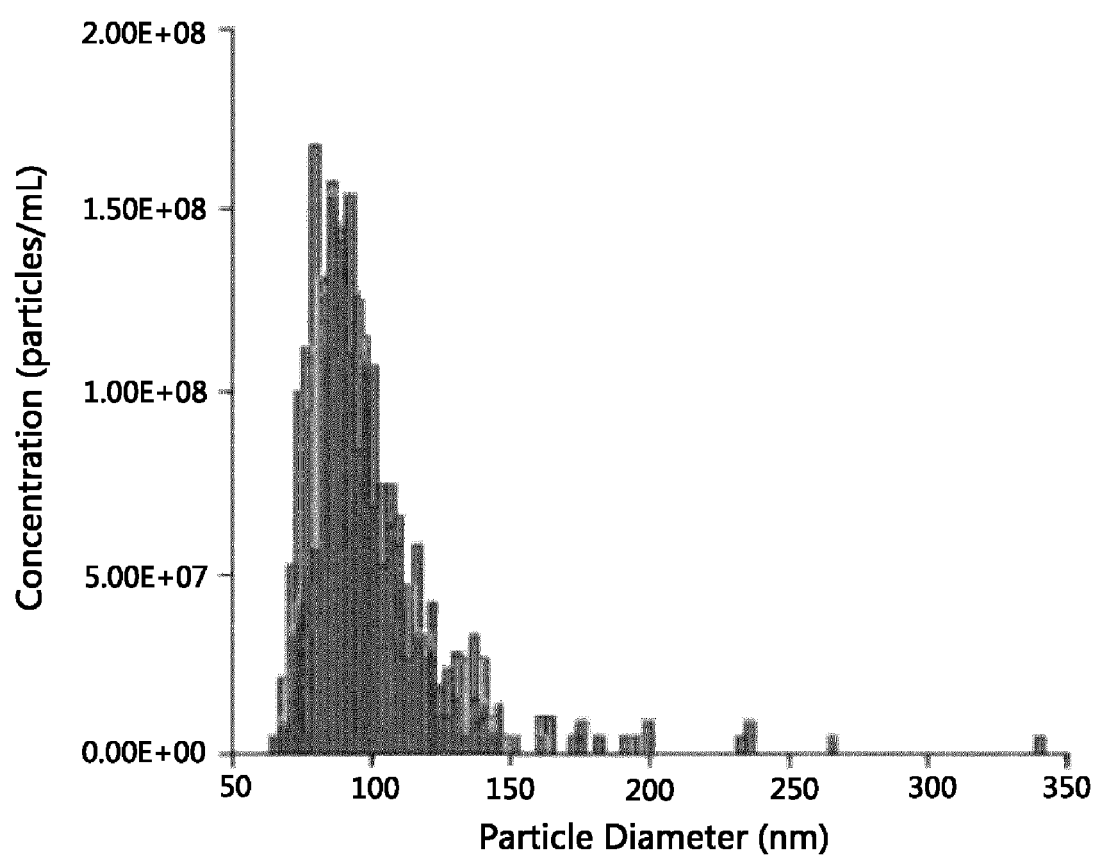
FIGS. 4A to 4E show the results of analyzing the physical properties of exosomes obtained according to one embodiment of the present invention.
Figure 4B:
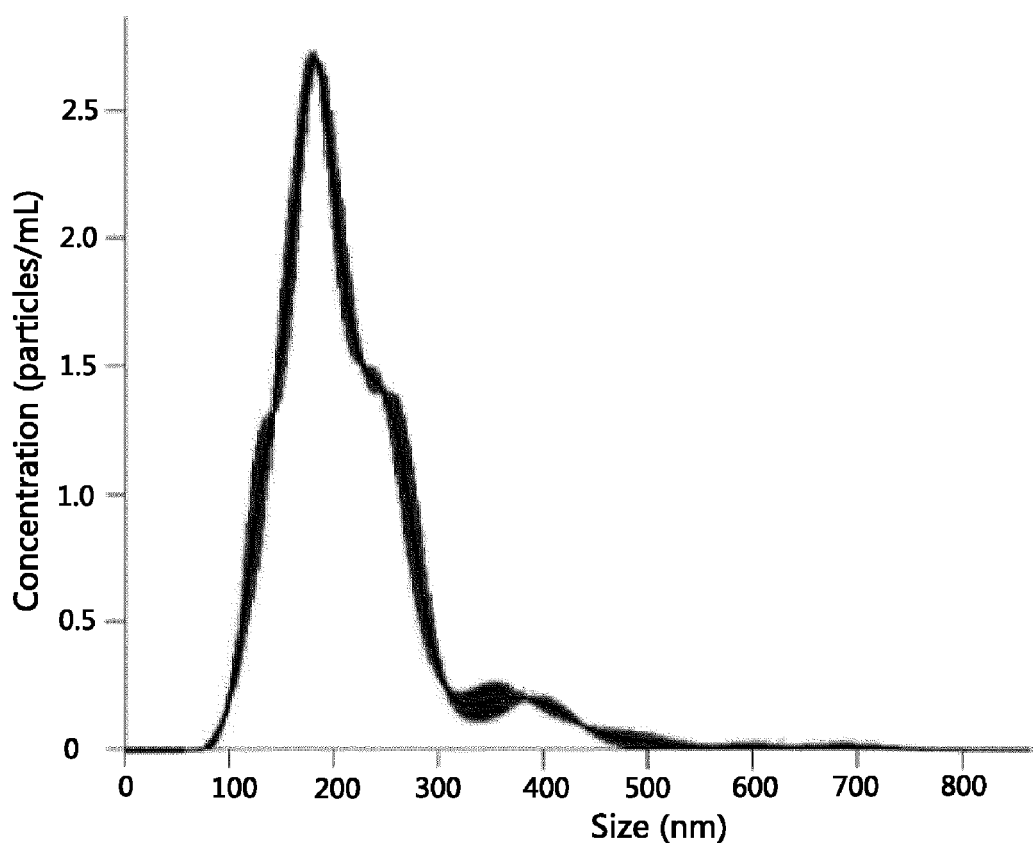
Figure 4C:
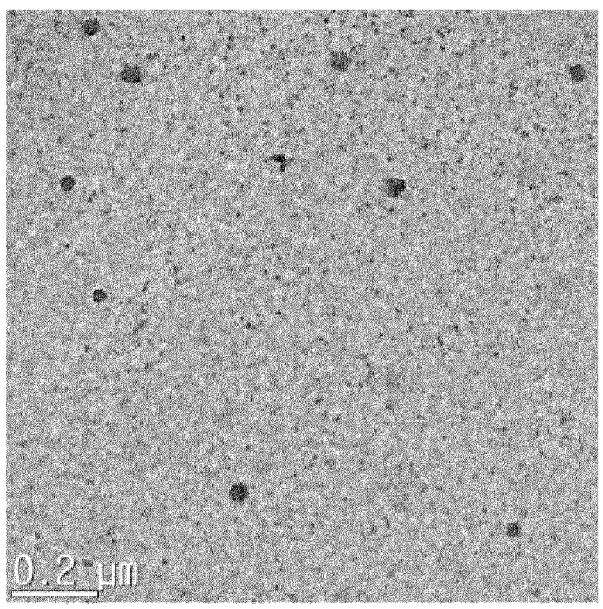
Figure 4C:
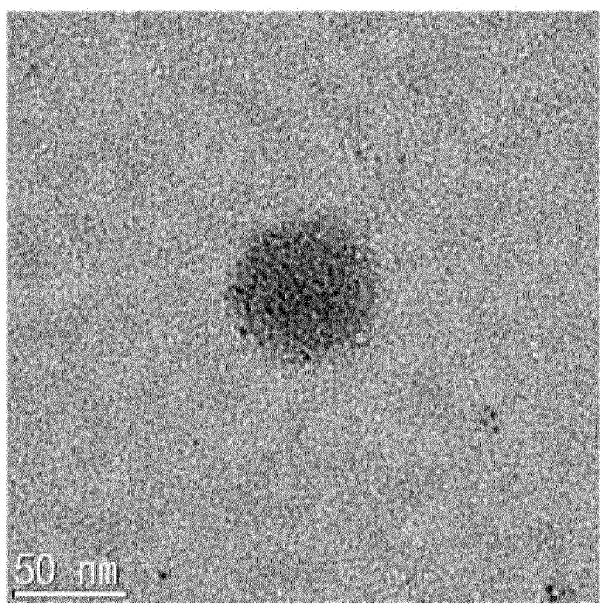

The particle size and concentration of the isolated exosomes were measured by nanoparticle tracking analysis (NTA) instrument (purchased from Malvern Panalytical) or tunable resistive pulse sensing (TRPS) instrument (purchased from Izon Science). The uniformity and size of the isolated exosomes were analyzed by transmission electron microscopy (TEM). FIGS. 4A to 4C show the results of TRPS, NTA and TEM of the exosomes isolated by the isolation method according to one embodiment of the present invention.

Figure 5A:
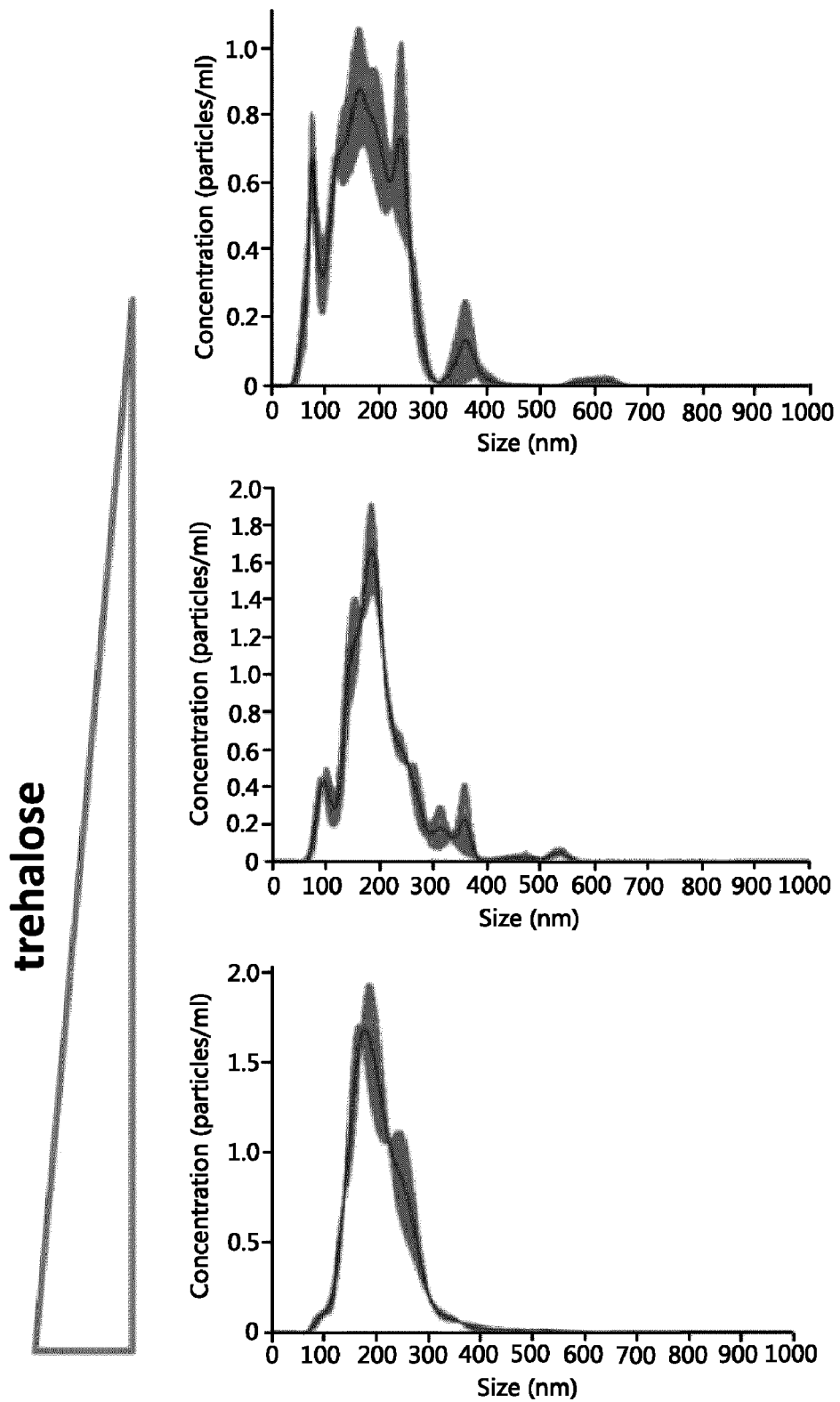
FIGS. 5A to 5C show the results of NTA analysis of particle size distributions, which indicate that exosomes having a uniform particle size distribution and high purity are obtained by the addition of trehalose. As the amount of trehalose added increases, a particle size distribution with a single peak can be obtained.
Figure 5B:
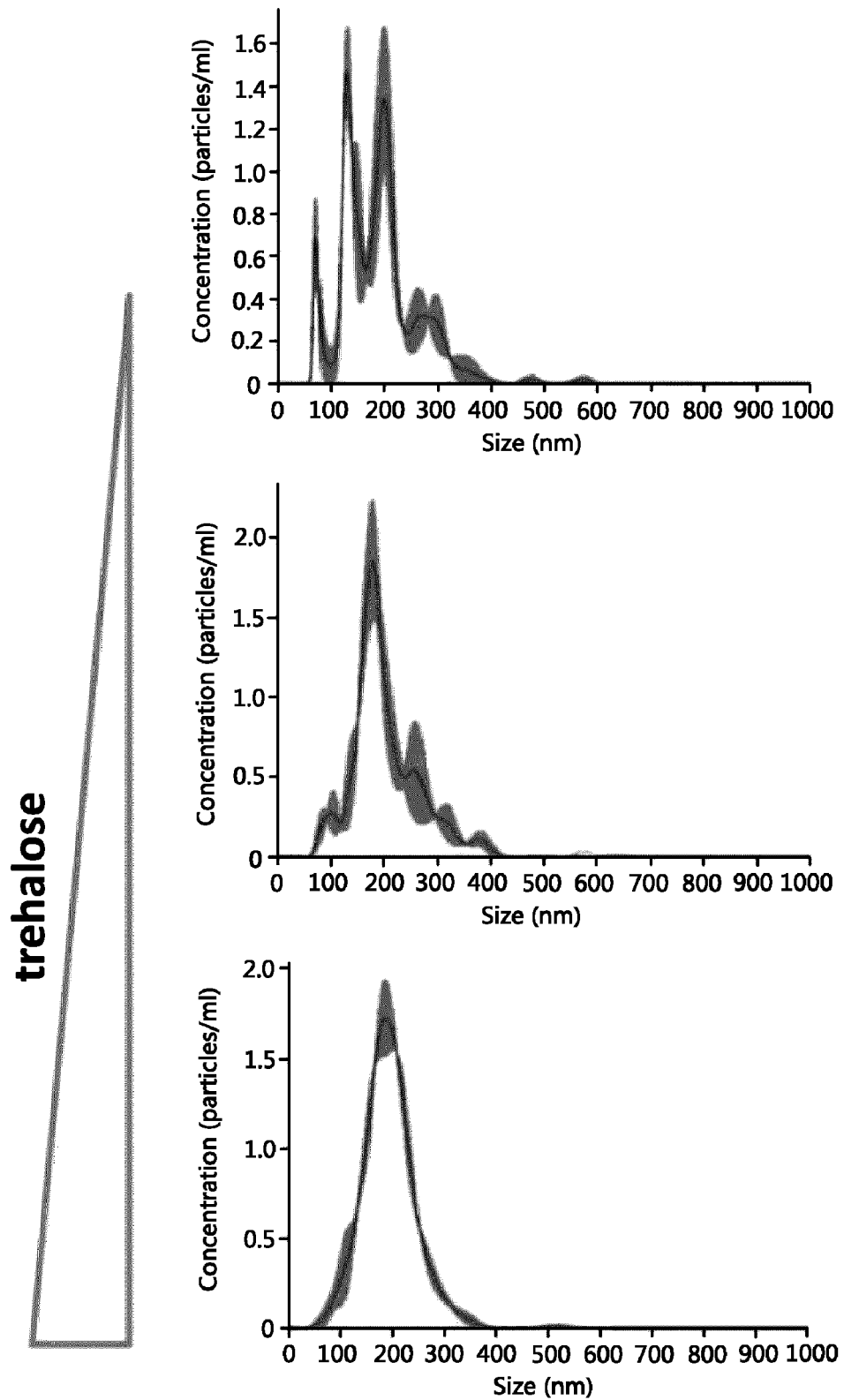
Figure 5C:
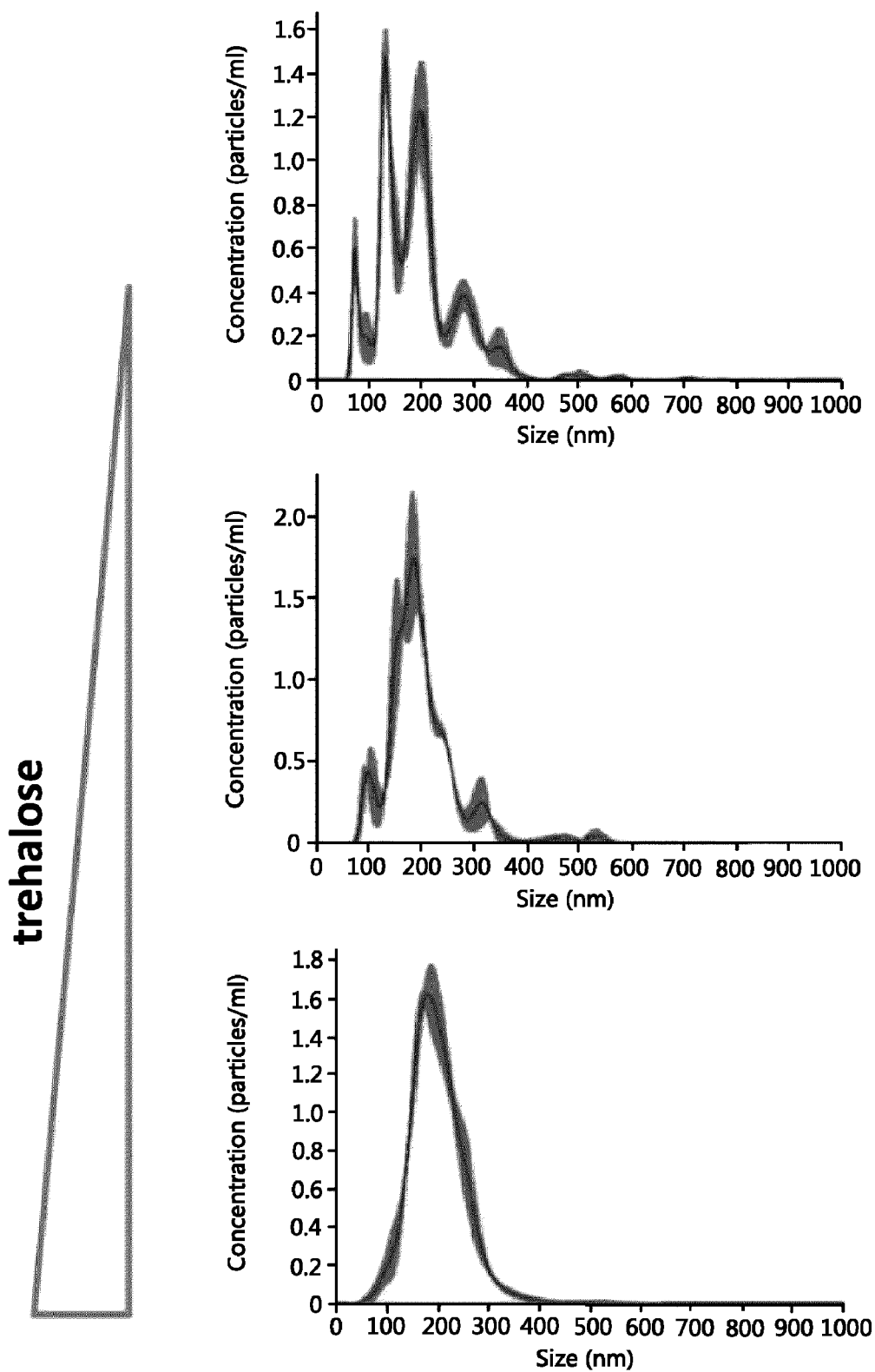

After exosomes were isolated by the TFF method, the size distribution of the exosomes was analyzed by NTA depending on whether trehalose was added. The results of the analysis are shown in FIGS. 5A to 5C. The concentration of trehalose was increased from 0 wt % to 1 wt % and 2 wt % (from the top to the bottom in FIGS. 5A to 5C), and the experiment was repeated three times. It was confirmed that when no trehalose was used, particles having a size of 300 nm or more were observed, whereas as the amount of trehalose added was increased, the number of particles having a size of 300 nm or more decreased and the size distribution of the exosomes became uniform.

Figure 6A:
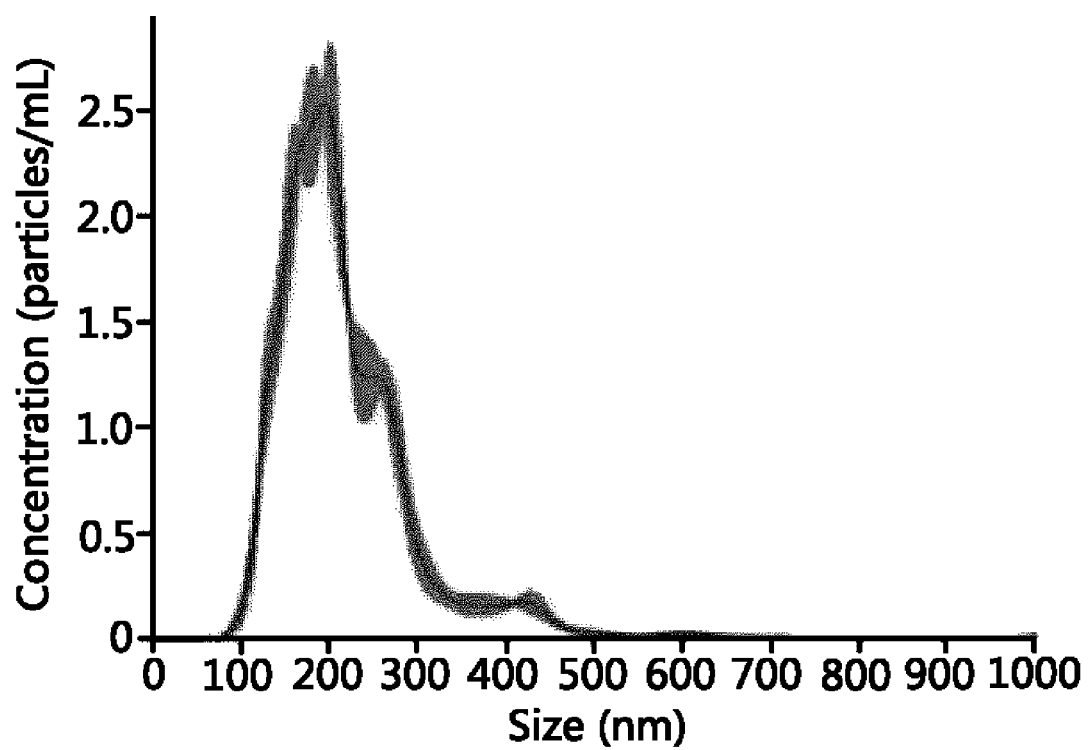
FIGS. 6A to 6C show the results of NTA analysis that indicate particle size distributions obtained depending on whether or not trehalose was added in a process of preparing exosomes according to one embodiment of the present invention.
Figure 6B:
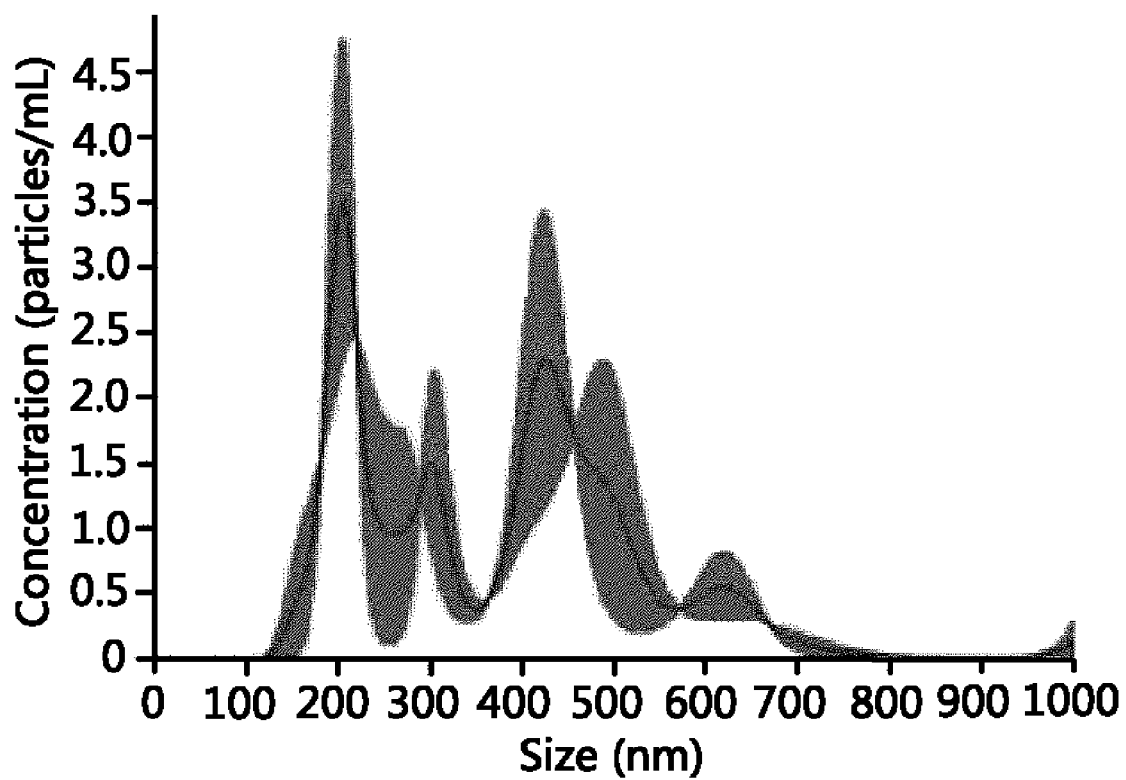
Figure 6C:
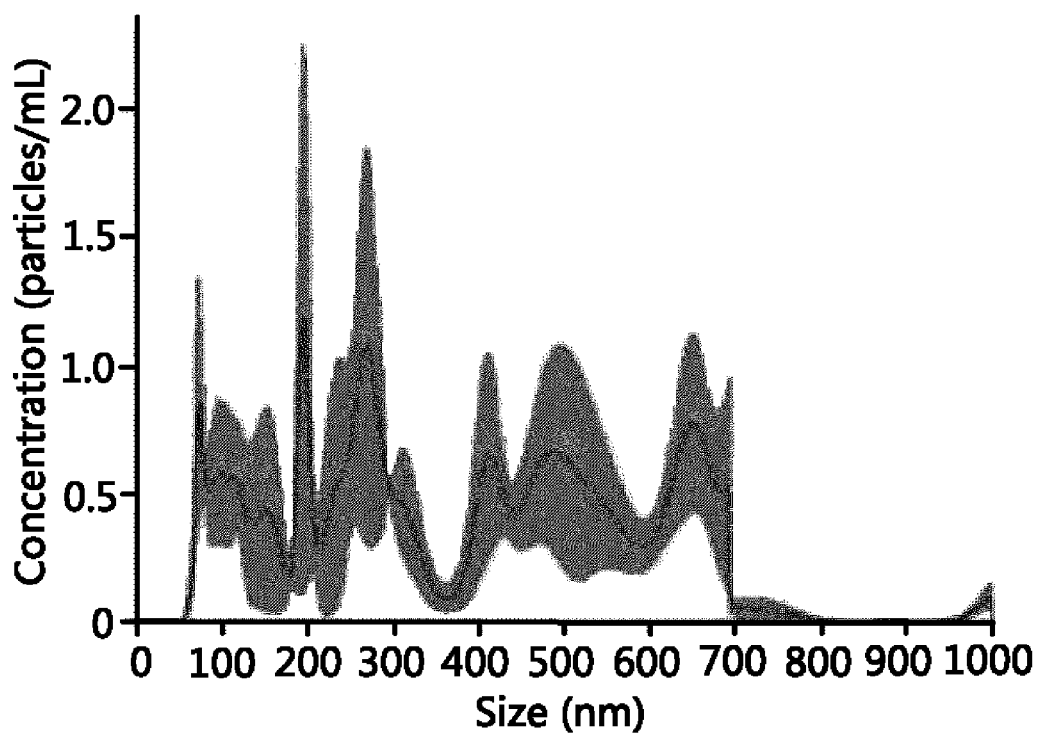

The effect due to the addition of trehalose in the process of isolating exosomes by the TFF method was additionally examined. As shown in FIGS. 6A to 6C, when 2 wt % trehalose in PBS was added throughout the process of preparing exosomes, exosomes having a uniform size distribution could be obtained (FIG. 6A). However, when the conditioned medium, which had been freeze-stored without adding trehalose, was used, but the TFF process was performed with adding trehalose only in the diafiltration process, or the TFF process was performed without adding any trehalose, uneven exosomes including a large amount of large particles were obtained (FIGS. 6B and 6C).

Figure 6D:
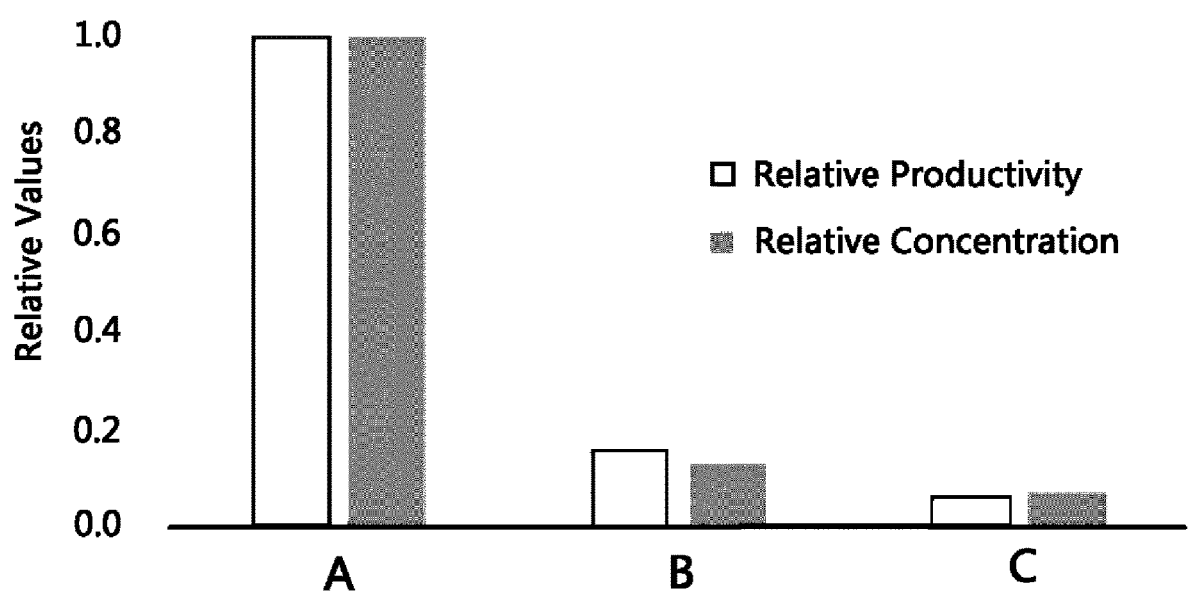
"FIG. 6D" shows the results of comparing the relative productivity and relative concentration of exosomes isolated by the methods of FIGS. 6A to 6C.
Figure 6E:
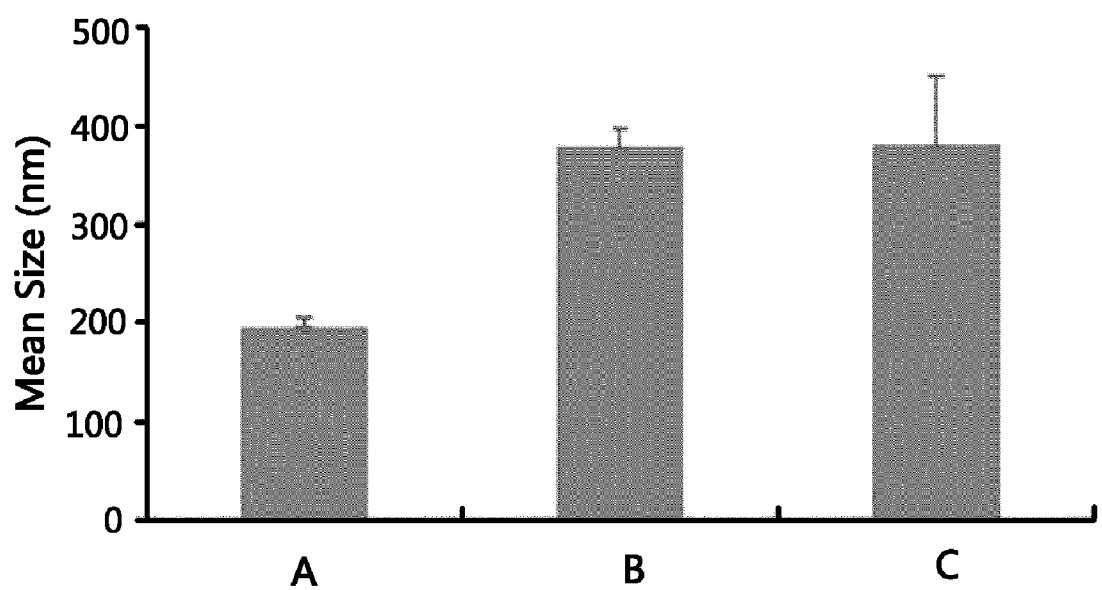
"FIG. 6E" shows the mean size of exosomes isolated by the methods of FIGS. 6A to 6C.

The relative productivity and concentration of the isolated exosomes were compared, and as a result, exosomes could be obtained with very high productivity when trehalose was added throughout the exosome production process. The obtained exosomes were at least 5 times concentration of the control (in which trehalose was not added throughout the exosome production process) (FIG. 6D). As shown in the NTA analysis results, it was confirmed that the mean size of the isolated exosomes was uniform (200 nm) when trehalose was added throughout the exosome production process (FIG. 6E).

Figure 4D:
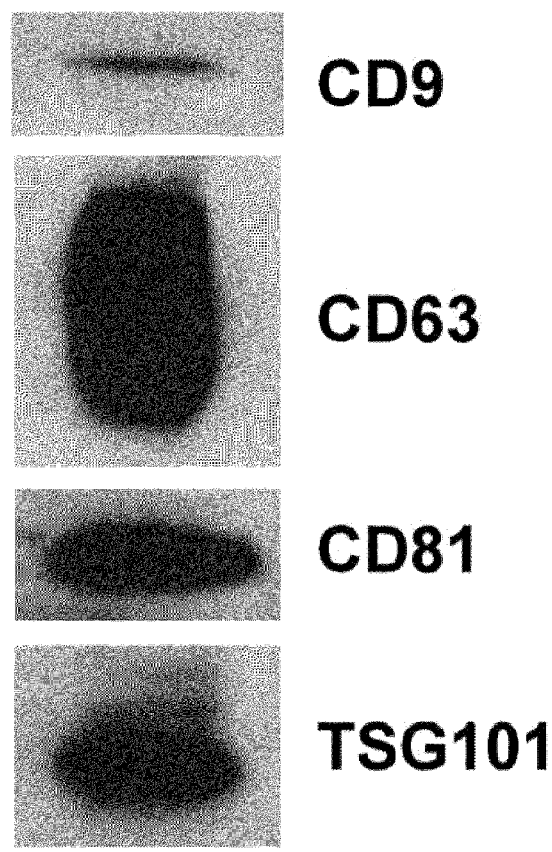

FIG. 4D shows the results of Western blot analysis of the exosomes isolated by the isolation method according to one embodiment of the present invention. As shown therein, the presence of CD9, CD63, CD81 and TSG101 markers was confirmed. As antibodies for each of the markers, anti-CD9 (purchased from Abcam), anti-CD63 (purchased from System Biosciences), anti-CD81 (purchased from System Biosciences), and anti-TSG101 (purchased from Abcam) were used, respectively.

Figure 4E:
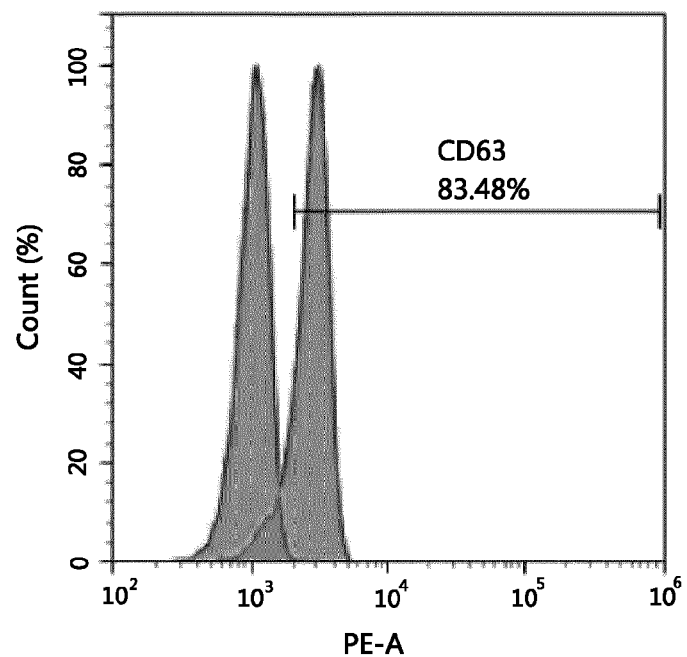
Figure 4E:
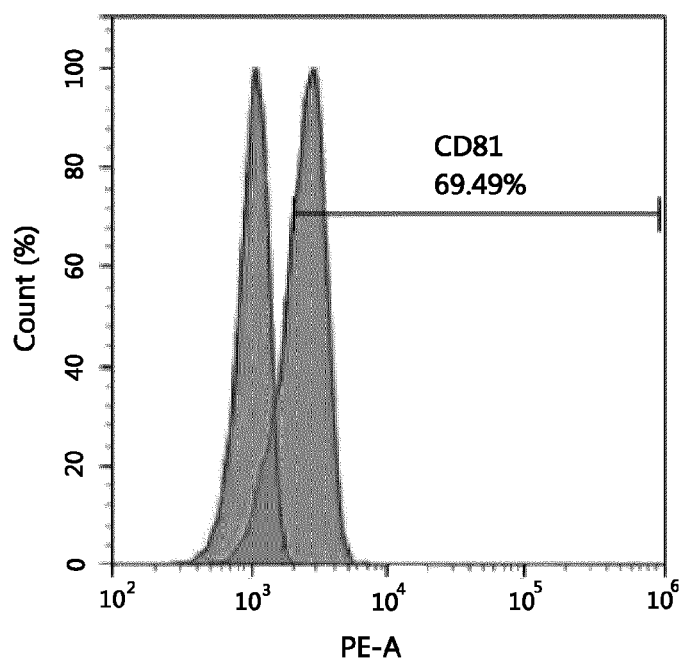

FIG. 4E shows the results of flow cytometry of the exosomes isolated by the isolation method according to one embodiment of the present invention. As shown therein, the presence of CD63 and CD81 markers was confirmed. To isolate CD63-positive exosomes, an Exosome-Human CD63 Isolation/Detection Reagent Kit (purchased from ThermoFisher Scientific) was used according to the manufacturer's instruction. The markers were stained with PE-Mouse anti-human CD63 (purchased from BD) or PE-Mouse anti-human CD81 (purchased from BD), and then analyzed using a flow cytometer (ACEA Biosciences).

Taking the above results together, it could be confirmed that the isolation method according to one embodiment of the present invention could economically and efficiently isolate and purify exosomes having a uniform particle size distribution and high purity in high yield by adding trehalose in the manufacturing process based on tangential flow filtration. In addition, it could be seen that the processes of the isolation method according to one embodiment of the present invention can be scaled-up and are also suitable for GMP.

Example 4: Measurement of Cytotoxicity Following Exosome Treatment

In order to evaluate the cytotoxicity of exosomes, isolated by the isolation method according to one embodiment of the present invention, on human dermal fibroblast Hs68 cells, the cells were treated with various concentrations of the exosomes, and the proliferation rate of the cells was examined. Hs68 cells were suspended in 10% FBS-containing DMEM, and then seeded and grown to 80 to 90% confluency and cultured in an incubator at 37° C. under 5% $CO_2$ for 24 hours. After 24 hours, the medium was removed, and the cells were treated with various concentrations of the exosomes prepared in Example 2. Then, the viability of the cells was evaluated while the cells were cultured for 24 to 72 hours. The cell viability was measured using WST-1 Cell Proliferation Assay System (purchased from Takara), MTT reagent (purchased from Sigma), CellTiter-Glo reagent (purchased from Promega) or alamarBlue Cell Viability Reagent (purchased from ThermoFisher Scientific) with a microplate reader (purchased from Molecular Devices).

Figure 7:
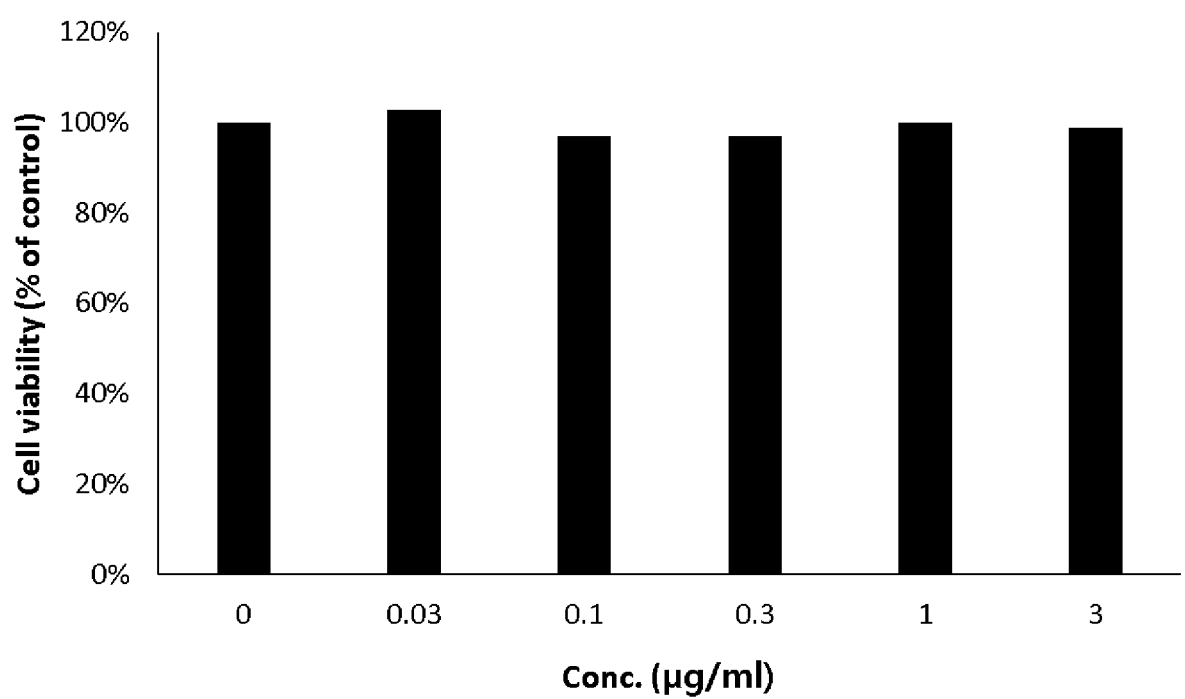
FIG. 7 shows results indicating that stem cell-derived exosomes according to one embodiment of the present invention were not cytotoxic after human fibroblast Hs68 cells were treated with the exosomes.

As a control, the cells cultured in conventional cell culture medium not treated with the exosomes was used. It was confirmed that the exosomes of the present invention showed no cytotoxicity in the concentration range used in the test (FIG. 7).

Example 5: Lyophilization of Exosomes

Example 5-1: Lyophilization Conditions

For lyophilization of exosomes, a cryoprotectant comprising methionine, mannitol and trehalose was prepared. An aqueous solution was prepared by adding the cryoprotectant to 1 mL of an aqueous solution containing 0.5 mg/mL each of ascorbic acid and retinol (prepared by BIO-FD&C Co., Ltd., Hwasun-gun, Jeollanam-do, Korea). Although the cryoprotectant was added to the solution containing ascorbic acid and retinol in this Example, an aqueous solution may also be prepared by adding the cryoprotectant to water for injection, purified water, physical saline, or deionized water. The concentration of each of methionine, mannitol and trehalose in the aqueous solution was adjusted to 9 mg/mL.

The exosomes ($5\times10^8$ particles/mL) prepared in Example 2 were mixed with the aqueous solution containing the cryoprotectant, and then lyophilized using a lyophilization system (manufactured by THE VIRTIS COMPANY, ITEM No.: 344424) under the conditions shown in Table 1 below. The lyophilization was performed in the order of conditions 1, 2, 3, 4, 5, 6, 7 and 8 as shown in Table 1 below.

TABLE 1

| Lyophilization conditions | | | |
| --- | --- | --- | --- |
| Total time (min) | | 4320 | |
| Conditions | Time (min) | Temperature (° C.) | Pressure (mmHg) |
| 1 | 700 | −50 | 760 |
| 2 | 60 | −50 | 760 |
| 3 | 999 | −50 | 0 |
| 4 | 999 | −50 | 0 |
| 5 | 999 | −50 | 0 |
| 6 | 370 | −50 | 0 |
| 7 | 120 | −20 | 0 |
| 8 | 73 | 10 | 0 |

Figure 8:
FIG. 8 depicts a photograph showing a good appearance of exosomes lyophilized according to one embodiment of the present invention.

After the exosomes were treated with the cryoprotectant comprising methionine, mannitol and trehalose, and lyophilized, the appearance thereof was examined. As a result, it can be seen that the exosomes were milky white in color and showed a good appearance which maintains a porous sponge shape (FIG. 8). That is, the method for lyophilizing exosomes according to the present invention is able to produce a lyophilized product having a good appearance by prolonging the drying time under vacuum and using the cryoprotectant having the combination of methionine, mannitol and trehalose.

Example 5-2: Comparison of Appearances of Lyophilized Exosomes Depending on Cryoprotectant Components Meanwhile, the appearances of exosomes lyophilized using various cryoprotectants comprising at least one of methionine, mannitol and trehalose (hereinafter, referred to as cryoprotectant components) were compared. According to the method described in Example 5-1 above, seven different aqueous solutions were prepared by adding the cryoprotectant components alone, combinations of two components, or a combination of three components. The concentration of each of the cryoprotectant components in each of the aqueous solutions was adjusted to 9 mg/mL. According to the lyophilization conditions and method described in Example 5-1 above, the exosomes ($5 \times 10^8$ particles) prepared in Example 2 above were mixed with the respective aqueous solution containing each of the cryoprotectant components alone, each of the combinations of two components, or the combination of three components, and then lyophilized.

The external appearances of the lyophilized exosome products were photographed and evaluated (FIGS. 9A to 9G). According to the states of the cake shapes of the lyophilized exosome products, the appearances of the lyophilized exosome products were ranked and relatively evaluated in a 5-point scale ranging from 1 (the worst cake appearance) to 5 (the best cake appearance). Table 2 below shows the results of evaluating the appearances of the lyophilized exosome products according to the combinations of the cryoprotectant components.

Comparison of appearances of lyophilized exosome products according to combinations of cryoprotectant components

Figure 9A:
FIGS. 9A to 9G are photographs each of which shows, after performing lyophilization using different combinations of cryoprotectant components, the appearance of lyophilized exosomes obtained according to each of the combinations of cryoprotectant components.
Figure 9B:
Figure 9C:
Figure 9D:
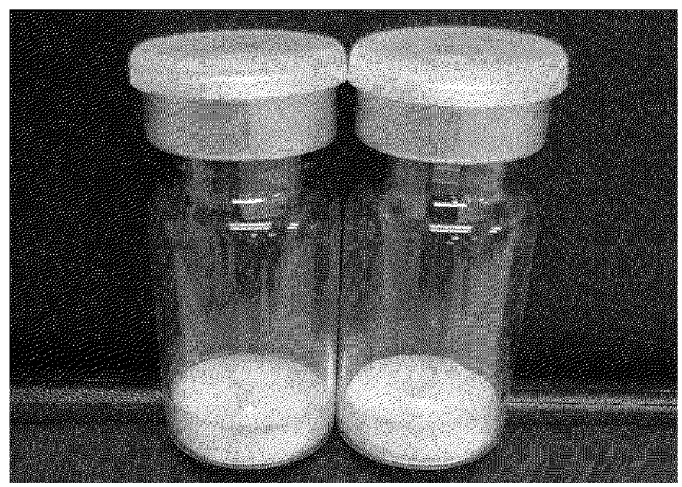
Figure 9E:
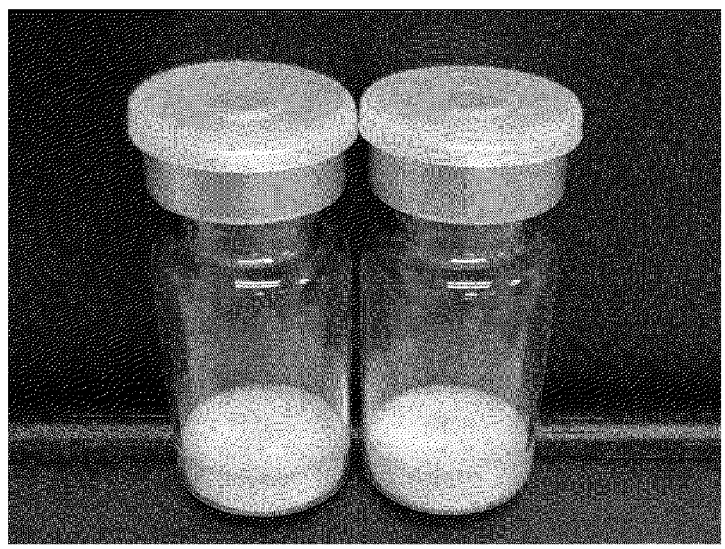
Figure 9F:
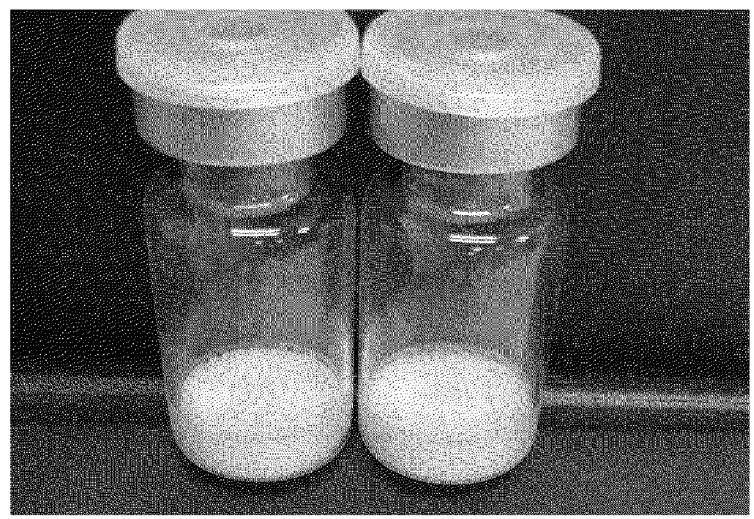
Figure 9G:
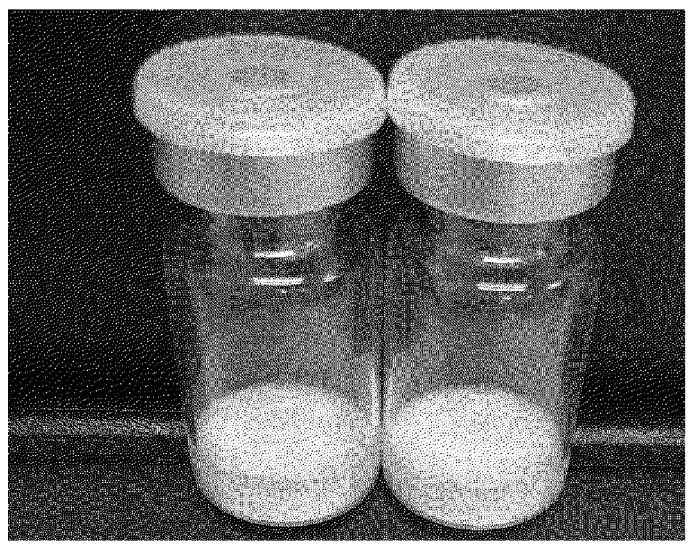

| Composition of cryoprotectant components | Mannitol | Trehalose | Methionine | Methionine + Trehalose | Methionine + Mannitol | Trehalose + Mannitol | Methionine + Mannitol + Trehalose (present invention) |
|---|---|---|---|---|---|---|---|
| Evaluated score | 1 | 1 | 4 | 3 | 4 | 2 | 5 |
| FIGS. | FIG. 9A | FIG. 9B | FIG. 9C | FIG. 9D | FIG. 9E | FIG. 9F | FIG. 9G |

As shown in FIGS. 9A to 9G and Table 2 above, it can be seen that the product obtained by lyophilizing exosomes using the cryoprotectant having the combination of methionine, mannitol and trehalose has the best external appearance, however, the external appearances of the products obtained by lyophilizing exosomes using the one component or the combinations of the two components are poorer than that of the product of the present invention.

Example 6: First Facial Clinical Testing of Composition for Alleviating Facial Redness Human faces were irradiated with an Erbium Fraxel laser using the Er:YAG laser system JOULE™ (Sciton, Inc., California, USA) under the following laser parameter conditions: wavelength of 2940 nm; wavelength energy of 7 J/cm$^2$; 10×10 cm scanning mode; and 1 pass.

After the faces of subjects 1 and 2 were washed clean, an anesthetic was applied to the faces for 30 minutes, and the faces were irradiated with an Erbium Fraxel laser. After the redness of the faces was induced by laser beam irradiation, 1 ml of a suspension of exosomes (exosomes prepared in Example 2) at a concentration of $7.39 \times 10^8$ particles/mL was applied to the right half of the face of each subject, and a suitable amount of saline was applied to the left half of the face of each subject. Thereafter, a rubber mask was placed and pressed on the face of each subject for 30 minutes.

Figure 10A:
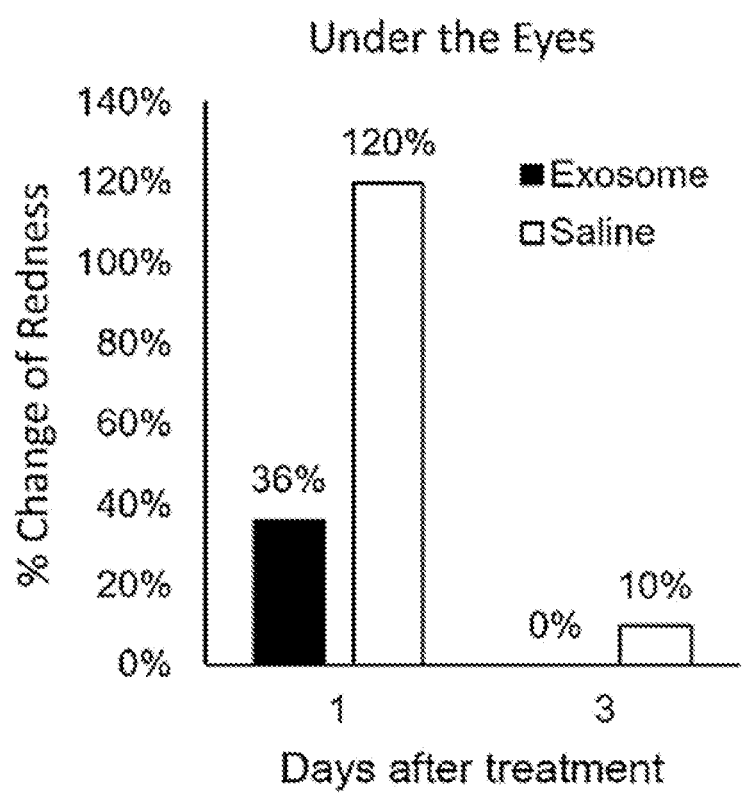
FIGS. 10A and 10B depict graphs showing the results of measuring facial redness at 1 and 3 days after applying the stem cell-derived exosomes according to one embodiment of the present invention and saline to the right and left haves, respectively, of the face of subject 1 having facial redness induced by an Er:Yag laser treatment.
Figure 10B:
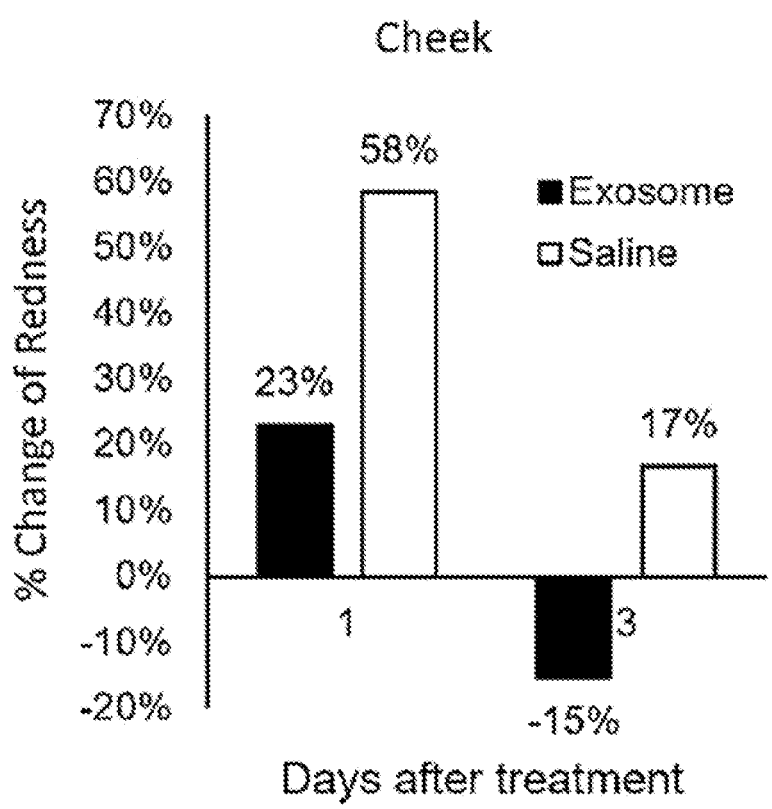

The redness of the face of each subject was measured using a MARK-VU™ facial skin analysis system (PSI Plus Co., Ltd., Gyeonggi-do, Korea). 1 and 3 days after the stem cell-derived exosomes and saline were applied to the right and left halves, respectively, of the face of subject 1 having facial redness induced by laser beam irradiation, the redness of the face was measured using the MARK-VU™ facial skin analysis system. The % change of the redness measured in each area was calculated using the following equation: % Change of redness=[(redness measured at N days)−(redness before treatment)]/(redness before treatment). From all the results measured at 1 and 3 days, it could be confirmed that the redness of each of the area under the right eye and the right cheek area, treated with the stem cell-derived exosomes, was remarkably reduced, as compared with the redness of each of the area under the left eye and the left cheek area, which are the facial areas to which saline was applied (FIGS. 10A and 10B).

Figure 11:
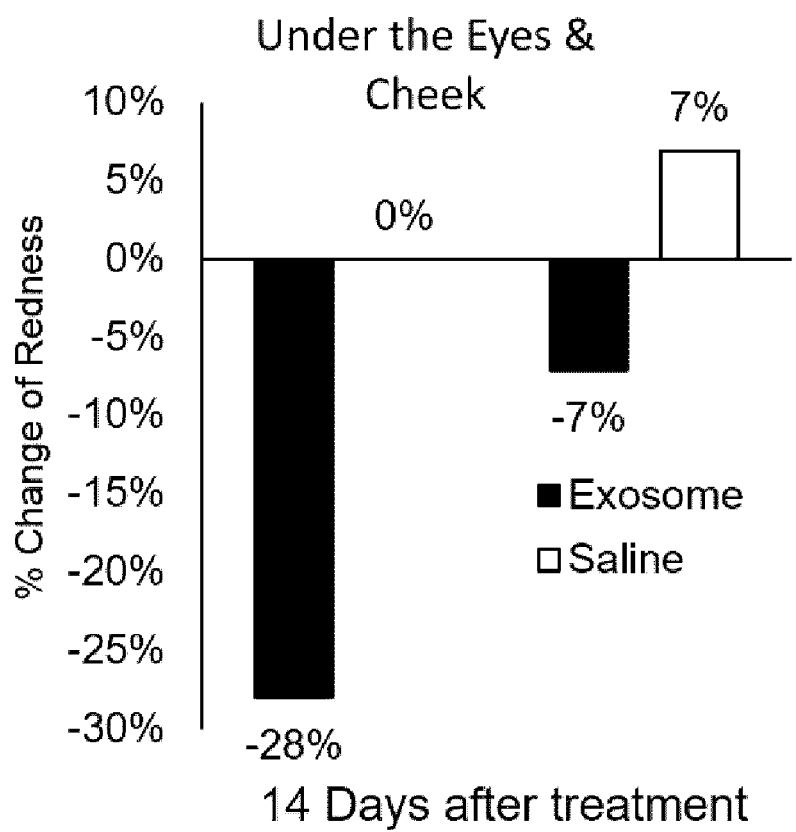
FIG. 11 is a graph showing the results of measuring redness under the eyes and redness of the cheeks at 14 days after applying the stem cell-derived exosomes according to one embodiment of the present invention and saline to the right and left halves, respectively, of the face of subject 2 having facial redness induced by an Er:Yag laser treatment.

In addition, in the same manner as described above, 14 days after the stem cell-derived exosomes and saline were applied to the right and left halves, respectively, of the face of subject 2 having facial redness induced by laser beam irradiation, the redness of the face was measured using the MARK-VU™ facial skin analysis system. As a result, it could be confirmed that the redness of each of the area under the right eye and the right cheek area, treated with the stem cell-derived exosomes, was remarkably reduced, as compared with the redness of each of the area under the left eye and the left cheek area, which are the facial areas to which saline was applied (FIG. 11).

Taking the above-described test results together, it can be seen that when a face is treated with the composition for alleviating facial redness containing stem cell-derived exosomes as an active ingredient, the composition remarkably reduces the laser-induced redness of the face. This means that the composition for alleviating facial redness according to the present invention is able to exhibit a skin care effect by improving the appearance of the face through the alleviation of facial redness.

Example 7: Second Facial Clinical Testing of Composition for Alleviating Facial Redness A lyophilized product (lyophilized exosomes prepared in Example 5-1) containing stem cell-derived exosomes at a concentration of $5 \times 10^8$ particles/vial was mixed with purified water, thus preparing 2 mL of an aqueous solution. The prepared composition for alleviating facial redness containing stem cell-derived exosomes was applied to the facial areas of subjects 3 to 5 having facial redness symptoms, in two sessions two weeks apart, by a microneedle therapy system (MTS) mounted with very thin needles. As an MTS, MY-M was used (purchased from Bomtech Electronics Co., Ltd., Gangseo-gu, Seoul, Korea).

Meanwhile, in this Example, the aqueous solution obtained by mixing the lyophilized exosomes prepared in Example 5-1 with purified water was used as the composition for alleviating facial redness, but alternatively, a suspension obtained by suspending, in water for injection, the exosomes (for example, an exosome concentration of $1 \times 10^8$ particles/mL or more) prepared in Example 2, may also be used as the composition for alleviating facial redness.

The redness of the face of each subject was measured using a MARK-VU™ facial skin analysis system (PSI Plus Co., Ltd., Gyeonggi-do, Korea). The % change of the redness measured in each of facial areas (forehead, nasal ridge, areas under left and right eyes, and left and right cheeks) was calculated using the equation described in Example 6.

Figure 12:
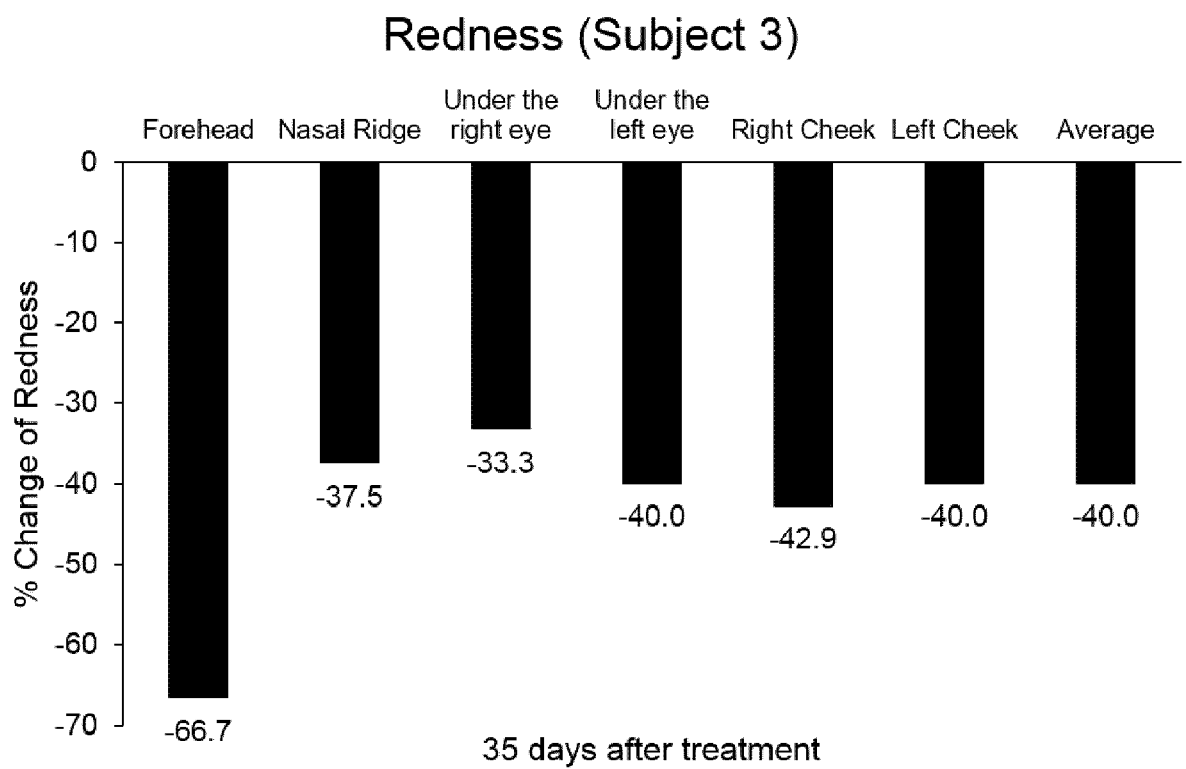
FIG. 12 is a graph showing the results of measuring facial redness at 35 days after treating the face of subject 3 with the composition for alleviating facial redness containing stem cell-derived exosomes as an active ingredient according to one embodiment of the present invention.
Figure 13:
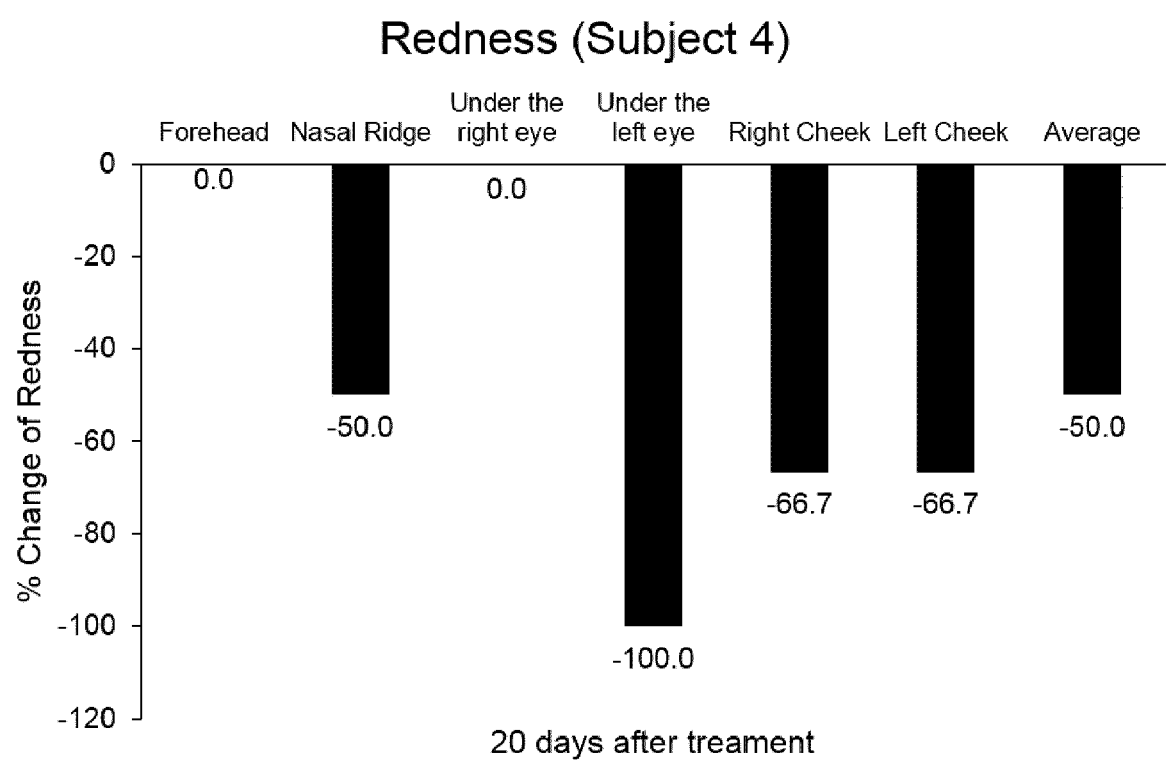
FIG. 13 is a graph showing the results of measuring facial redness at 20 days after treating the face of subject 4 with the composition for alleviating facial redness containing stem cell-derived exosomes as an active ingredient according to one embodiment of the present invention.
Figure 14:
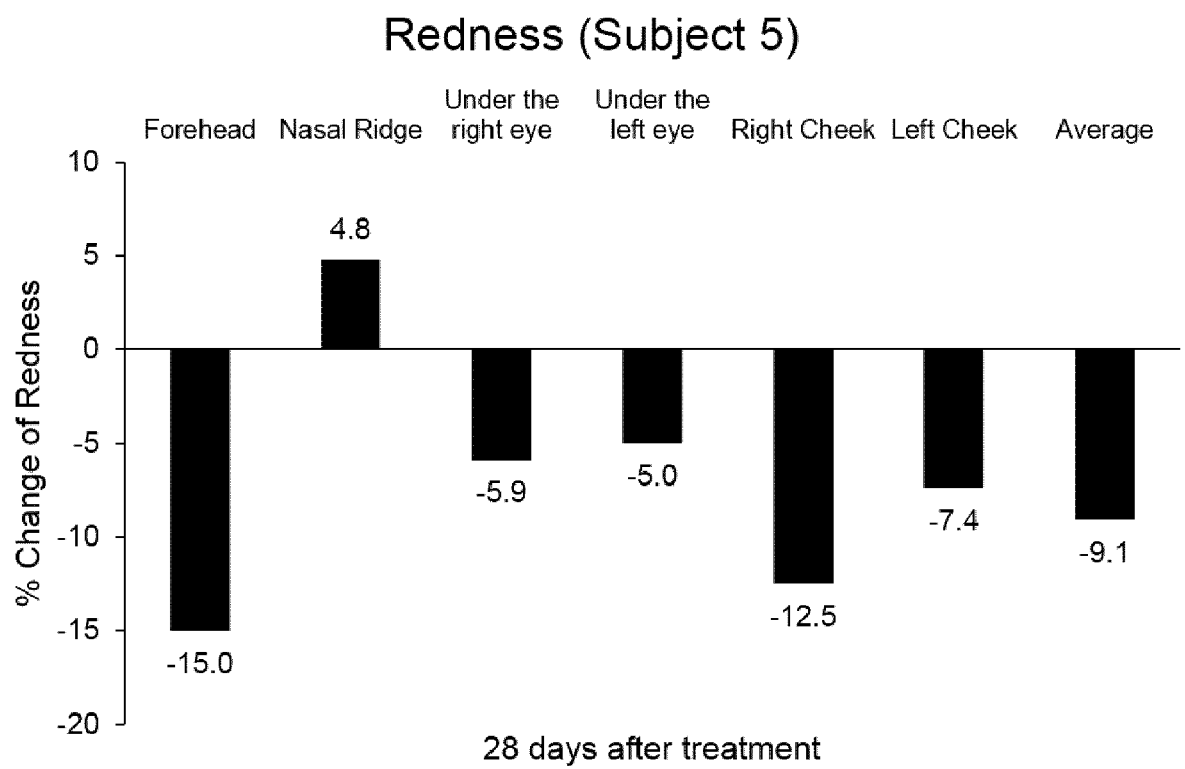
FIG. 14 is a graph showing the results of measuring facial redness at 28 days after treating the face of subject 5 with the composition for alleviating facial redness containing stem cell-derived exosomes as an active ingredient according to one embodiment of the present invention.

In the case of subject 3, it was confirmed that 35 days after treatment with the composition, the redness of the face was remarkably reduced in all the forehead, the nasal ridge, the areas under the left and right eyes, and the left and right cheeks, as compared with the redness of the face before treatment with the composition (FIG. 12). In addition, in the case of subject 4, it was confirmed that 20 days after treatment with the composition, the redness of the face was remarkably reduced in the nasal ridge, the area under the left eye, and the left and right cheeks, as compared with the redness of the face before treatment with the composition (FIG. 13). In the case of subject 5, it was confirmed that 28 days after treatment with the composition, the redness of the face was remarkably reduced in the forehead, the areas under the left and light eyes, and the left and right cheeks, as compared with the redness of the face before treatment with the composition (FIG. 14).

Taking the above-described test results together, it can be seen that when a facial skin is treated with the composition for alleviating facial redness containing stem cell-derived exosomes as an active ingredient, the composition remarkably reduces the redness of the face, and is able to exhibit a skin care effect by improving the appearance of the face through the alleviation of facial redness.

Figure 15:
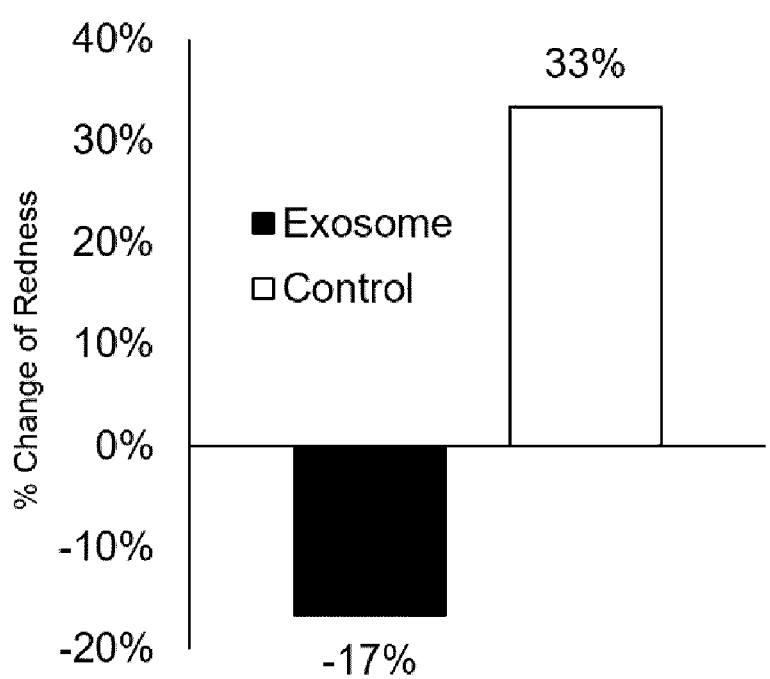
FIG. 15 is a graph showing the results of measuring facial redness after applying the stem cell-derived exosomes according to one embodiment of the present invention to the right half of the face of subject 6 having facial redness induced by Er:Yag laser beam irradiation and then performing iontophoresis on the right half of the face for 15 minutes, and merely applying a rubber mask (control) to the left half of the face.

Example 8: Third Facial Clinical Testing of Composition for Alleviating Facial Redness In the same manner as described in Example 6, facial redness was induced in subject 6, and then the stem cell-derived exosomes (at a concentration of $7.39 \times 10^8$ particles/mL) according to one embodiment of the present invention were applied to the right half of the face of subject 6. Iontophoresis was performed on the right half of the face for 15 minutes, and a rubber mask was placed and pressed on the left half of the face for 15 minutes. The iontophoresis was performed by applying a micro-current of 0.5 mA to the right facial half, to which the stem cell-derived exosomes were applied, for 15 minutes by an iontophoresis system (IONZYME®, Environ). According to the method described in Example 6, the redness of each of the right and left halves of the face was measured before and after the treatment and compared with each other. As a result, it was confirmed that, when iontophoresis was performed after the stem cell-derived exosomes were applied to the face, the redness of the face was immediately and remarkably reduced, as compared with the redness of the face measured when the rubber mask was simply placed and pressed (FIG. 15).

According to the above-described test results, it can be seen that, when the facial skin is treated with the composition for alleviating facial redness containing stem cell-derived exosomes as an active ingredient and then iontophoresis is performed on the treated facial skin, the redness of the face can be immediately and remarkably reduced, and the effect for improving the appearance of the face is maximized.

Example 9: Fourth Facial Clinical Testing of Composition for Alleviating Facial Redness Facial redness was induced by irradiating a human face with a Pico laser using the Pico laser system PICOPLUS™ (Lutronic Co., Ltd., Gyeonggi-do, Korea) under the following laser parameter conditions: wavelength of 1064 nm; wavelength energy of 0.7 J/cm$^2$; laser spot size of 7 mm; laser irradiation time of 450 ps (picosecond); frequency of 10 Hz; laser irradiation of 3,000 shots.

After the face of subject 7 was washed clean, an anesthetic was applied to the face for 30 minutes, and the face was irradiated with a Pico laser. After the redness of the face was induced by laser beam irradiation, 1 ml of a suspension of exosomes (exosomes prepared in Example 2) at a concentration of $7.39 \times 10^8$ particles/mL was applied to the right half of the face of subject 7, and a suitable amount of a vitamin C solution (1% vitamin phosphate solution) was applied to the left half of the face of subject 7. Thereafter, iontophoresis was performed on each of the right and left halves of the face of subject 7. The iontophoresis was performed by applying a micro-current of 0.5 mA to the right facial half, to which the stem cell-derived exosomes were applied, for 20 minutes by an iontophoresis system (IONZYME®, Environ).

Figure 16:
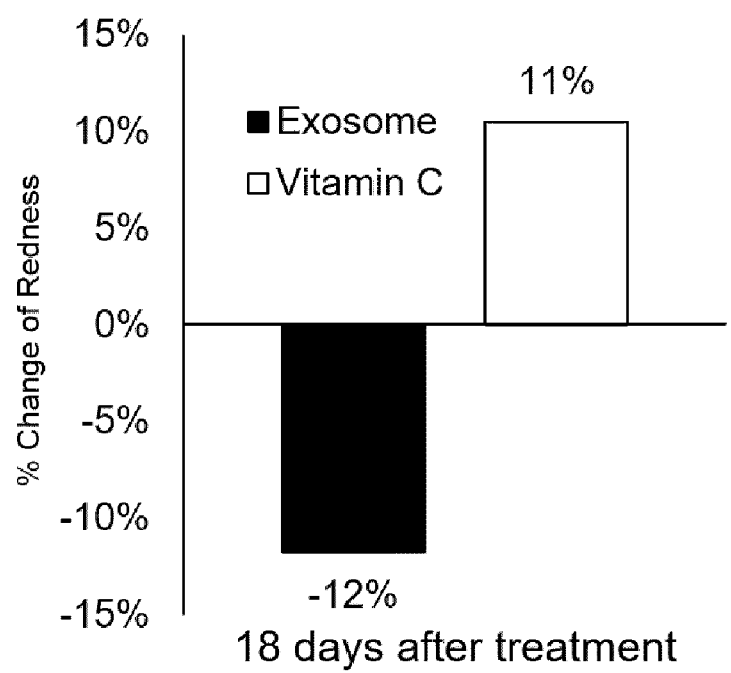
FIG. 16 is a graph showing the results of measuring facial redness at 18 days after applying the stem cell-derived exosomes according to one embodiment of the present invention and vitamin C to the right and left halves, respectively, of the face of subject 7 having facial redness induced by Pico laser beam irradiation and additionally performing iontophoresis on the face.

18 days after the face was treated as described above, the redness of the facial areas was measured using a Mark-Vu facial skin analysis system in the same manner as in Example 6 and compared. As a result, the effect of alleviating facial redness was more remarkable in the right facial half treated with the composition for alleviating facial redness containing stem cell-derived exosomes than in the left facial half treated with the control vitamin C (FIG. 16).

Although the present invention has been described with reference to the embodiments, the scope of the present invention is not limited to these embodiments. Any person skilled in the art will appreciate that various modifications and changes are possible without departing from the spirit and scope of the present invention and these modifications and changes also fall within the scope of the present invention.

We claim:

1. A method for preventing, suppressing, alleviating, ameliorating or treating facial redness of a subject, the method comprising steps of:
   (a) preparing a composition containing isolated exosomes derived from adipose-derived stem cells, wherein the composition does not include adipose-derived stem cells, and the exosomes are isolated from a conditioned medium of the adipose-derived stem cells; and
   (b) treating a facial skin of the subject, which has facial redness, with the composition.

2. The method of claim 1, wherein the composition is administered to the facial skin by microneedling, iontophoresis or injection.

3. The method of claim 1, further comprising steps of:
   (c) performing iontophoresis by allowing a microcurrent to flow through the facial skin treated with the composition; and
   (d) delivering the exosomes inside the facial skin by the microcurrent.

4. The method of claim 3, wherein the composition is used in one or more form selected from the group consisting of a patch, a mask pack, a mask sheet, a cream, a tonic, an ointment, a suspension, an emulsion, a paste, a lotion, a gel, an oil, a spray, an aerosol, a mist, a foundation, a powder, and an oilpaper.

5. The method of claim 4, wherein the composition is applied to or soaked in a surface of the patch, the mask pack, or the mask sheet.

6. The method of claim 5, wherein step (b) is performed by:
(b1) applying the composition directly to the facial skin; or
(b2) contacting or attaching the mask pack, the mask sheet, or the patch, which has the composition applied thereto or soaked therein, to the facial skin; or
(b3) sequentially performing (b1) and (b2).

7. The method of claim 6, wherein step (c) is performed by contacting or attaching an iontophoresis device to the facial skin.

8. The method of claim 7, wherein the iontophoresis device comprises at least one battery selected from the group consisting of flexible batteries, lithium-ion secondary batteries, alkaline batteries, dry cells, mercury batteries, lithium batteries, nickel-cadmium batteries, and reverse electrodialysis batteries.

9. The method of claim 1, wherein the composition comprises a lyophilized formulation comprising: as active ingredients, the isolated exosomes derived from adipose-derived stem cells; and methionine, mannitol, and trehalose.

10. The method of claim 9, wherein the lyophilized formulation further comprises ascorbic acid and retinol.

11. The method of claim 9, wherein the composition further comprises a diluent.

12. The method of claim 11, wherein the diluent comprises water for injection, physiological saline, phosphate buffered saline, purified water, or deionized water.

13. The method of claim 12, wherein the diluent further comprises hyaluronic acid or hyaluronate.

14. The method of claim 11, wherein the composition is prepared as a suspension.

15. The method of claim 14, wherein the composition is an injectable formulation.

16. A method for preventing, suppressing, alleviating, ameliorating or treating facial redness of a subject, the method comprising steps of:
(a) preparing a composition containing isolated exosomes derived from adipose-derived stem cells, wherein the composition does not include adipose-derived stem cells, and the exosomes are isolated from a conditioned medium of the adipose-derived stem cells; and
(b) (b1) applying the composition directly to a facial skin of the subject, which has facial redness; or (b2) contacting or attaching a patch, a mask pack or a mask sheet, which has the composition applied thereto or soaked therein, to the facial skin; or (b3) sequentially performing (b1) and (b2).

17. The method of claim 16, wherein the composition comprises a lyophilized formulation comprising: as active ingredients, the isolated exosomes derived from adipose-derived stem cells; and methionine, mannitol, and trehalose.

18. The method of claim 17, wherein the lyophilized formulation further comprises ascorbic acid and retinol.

19. The method of claim 17, wherein the composition further comprises a diluent.

20. The method of claim 19, wherein the diluent comprises water for injection, physiological saline, phosphate buffered saline, purified water, or deionized water.

21. The method of claim 20, wherein the diluent further comprises hyaluronic acid or hyaluronate.

22. The method of claim 19, wherein the composition is prepared as a suspension.

23. The method of claim 16, further comprising step (c) removing the patch, the mask pack or the mask sheet from the facial skin after step (b), and applying the composition to the facial skin.

24. A skin care method comprising steps of:
(a) irradiating facial skin of a subject with an Er:Yag laser beam to induce facial redness; and
(b) applying a composition containing isolated exosomes derived from adipose-derived stem cells to the facial skin, wherein the composition does not include adipose-derived stem cells, and the exosomes are isolated from a conditioned medium of the adipose-derived stem cells;
wherein the facial redness induced by the Er:Yag laser beam irradiation is reduced by applying the composition of step (b).

25. The method of claim 24, wherein the composition comprises a lyophilized formulation comprising: as active ingredients, the isolated exosomes derived from adipose-derived stem cells; and methionine, mannitol, and trehalose.

26. The method of claim 25, wherein the lyophilized formulation further comprises ascorbic acid and retinol.

27. The method of claim 25, wherein the composition further comprises a diluent.

28. The method of claim 27, wherein the diluent comprises water for injection, physiological saline, phosphate buffered saline, purified water, or deionized water.

29. The method of claim 28, wherein the diluent further comprises hyaluronic acid or hyaluronate.

30. The method of claim 27, wherein the composition is prepared as a suspension.

31. The method of claim 24, further comprising steps of:
(c) performing iontophoresis by allowing a microcurrent to flow through the skin to which the composition has been applied; and
(d) delivering the composition inside the skin by the microcurrent.

32. The method of claim 31, wherein the composition is used in one or more form selected from the group consisting of a patch, a mask pack, a mask sheet, a cream, a tonic, an ointment, a suspension, an emulsion, a paste, a lotion, a gel, an oil, a spray, an aerosol, a mist, a foundation, a powder, and an oilpaper.

33. The method of claim 32, wherein the composition is applied to or soaked in a surface of the patch, the mask pack, or the mask sheet.

34. The method of claim 33, wherein step (b) is performed by:
(b1) applying the composition directly to the skin; or
(b2) contacting or attaching the mask pack, the mask sheet, or the patch, which has the composition applied thereto or soaked therein, to the skin; or
(b3) sequentially performing (b1) and (b2).

35. The method of claim 34, wherein step (c) is performed by contacting or attaching an iontophoresis device to the skin.

36. The method of claim 35, wherein the iontophoresis device comprises at least one battery selected from the group consisting of flexible batteries, lithium-ion secondary batteries, alkaline batteries, dry cells, mercury batteries, lithium batteries, nickel-cadmium batteries, and reverse electrodialysis batteries.

* * * * *